US011633357B2

(12) United States Patent
Richter et al.

(10) Patent No.: US 11,633,357 B2
(45) Date of Patent: *Apr. 25, 2023

(54) LIPOSOME FORMULATION AND MANUFACTURE

(71) Applicant: Zuli Holdings Ltd., Tel Aviv (IL)

(72) Inventors: Yoram Richter, Ramat Hasharon (IL); Yehuda Zelig, Ness Ziona (IL); Omar Elmalak, Jat Village (IL); Dror Eyal, Ness Ziona (IL)

(73) Assignee: ZULI HOLDINGS, LTD., Tel Aviv (IL)

( * ) Notice: Subject to any disclaimer, the term of this patent is extended or adjusted under 35 U.S.C. 154(b) by 403 days.

This patent is subject to a terminal disclaimer.

(21) Appl. No.: 16/289,775

(22) Filed: Mar. 1, 2019

(65) Prior Publication Data
US 2019/0192434 A1    Jun. 27, 2019

Related U.S. Application Data

(63) Continuation of application No. 15/974,817, filed on May 9, 2018, now Pat. No. 10,265,269, which is a
(Continued)

(51) Int. Cl.
*A61K 9/127*     (2006.01)
*A61K 9/00*      (2006.01)
*A61K 47/24*     (2006.01)

(52) U.S. Cl.
CPC ............ *A61K 9/127* (2013.01); *A61K 9/0019* (2013.01); *A61K 47/24* (2013.01)

(58) Field of Classification Search
CPC ....... A61K 9/127; A61K 9/0019; A61K 47/24
See application file for complete search history.

(56) References Cited

U.S. PATENT DOCUMENTS

| 4,067,971 A | 1/1978 | Francis et al. |
| 4,216,211 A | 8/1980 | Francis |

(Continued)

FOREIGN PATENT DOCUMENTS

| CA | 2459434 | 2/2003 |
| CN | 102805729 | 12/2012 |

(Continued)

OTHER PUBLICATIONS

Zdenka Šklubalová & Zdenek Zatloukal, *Conversion Between Osmolality and Osmolarity of Infusion Solutions*, 77 Sci. Pharm. 817-26 (2009), available at https://doi.org/10.3797/scipharm.0810-16.*

(Continued)

*Primary Examiner* — Gollamudi S Kishore
(74) *Attorney, Agent, or Firm* — Cadwalader, Wickersham & Taft LLP

(57) ABSTRACT

The present invention relates to a liposomal formulation containing a therapeutic agent and a process for producing the formulation. The liposomal formulation comprises particular characteristics that enhance uniformity and stability of the formulation. The manufacturing process is a novel process that produces a liposomal formulation of a uniform size with many desirable properties that may be independently controlled. Further, the invention relates to a liposome formulation made in accordance with the manufacturing process.

19 Claims, 5 Drawing Sheets

Related U.S. Application Data continuation of application No. 13/804,707, filed on Mar. 14, 2013, now Pat. No. 9,993,427.

(56) References Cited

U.S. PATENT DOCUMENTS

| | | | |
|---|---|---|---|
| 4,990,503 | A | 2/1991 | Isomura et al. |
| 4,997,454 | A | 3/1991 | Violanie et al. |
| 5,008,050 | A | 4/1991 | Cullis et al. |
| 5,096,717 | A | 3/1992 | Wirth et al. |
| 5,196,409 | A | 3/1993 | Breuer et al. |
| 5,312,954 | A | 5/1994 | Breuer et al. |
| 5,338,731 | A | 8/1994 | Breuer et al. |
| 5,356,887 | A | 10/1994 | Brener et al. |
| 5,492,926 | A | 2/1996 | Cullinan et al. |
| 5,527,538 | A | 6/1996 | Baldeschwieler |
| 5,652,227 | A | 7/1997 | Tanaka et al. |
| 5,681,817 | A | 10/1997 | Hodgen et al. |
| 5,733,564 | A | 3/1998 | Lehtinen |
| 5,741,514 | A | 4/1998 | Barenholz et al. |
| 5,746,223 | A | 5/1998 | Williams |
| 5,760,030 | A | 6/1998 | Bryant et al. |
| 5,776,429 | A | 7/1998 | Unger et al. |
| 5,792,885 | A | 8/1998 | Ham et al. |
| 5,820,879 | A | 10/1998 | Fernandez et al. |
| 5,877,284 | A | 3/1999 | Lyttle |
| 5,882,656 | A | 3/1999 | Bechard et al. |
| 5,932,563 | A | 8/1999 | Stokes et al. |
| 5,932,580 | A | 8/1999 | Levitzki et al. |
| 5,994,341 | A | 11/1999 | Hunter et al. |
| 6,030,639 | A | 2/2000 | Janoff et al. |
| 6,090,777 | A | 7/2000 | Hack et al. |
| 6,121,230 | A | 9/2000 | Charnock-Jones et al. |
| 6,121,278 | A | 9/2000 | Jackson et al. |
| 6,139,871 | A | 10/2000 | Hope et al. |
| 6,245,757 | B1 | 6/2001 | Chopp et al. |
| 6,306,421 | B1 | 10/2001 | Kunz et al. |
| 6,346,534 | B1 | 2/2002 | Zhu et al. |
| 6,432,413 | B1 | 8/2002 | Loeb |
| 6,719,998 | B1 | 4/2004 | Golomb et al. |
| 6,770,466 | B2 | 8/2004 | Shi et al. |
| 6,984,400 | B2 | 1/2006 | Golomb et al. |
| 7,008,645 | B2 | 3/2006 | Golomb et al. |
| 9,226,984 | B2 * | 1/2016 | Petersen ............ A61K 51/0482 |
| 2001/0031741 | A1 | 10/2001 | Ziegler et al. |
| 2002/0025313 | A1 | 2/2002 | Micklus et al. |
| 2002/0110588 | A1 | 8/2002 | Hope et al. |
| 2002/0160495 | A1 | 10/2002 | Mirochnitchenko et al. |
| 2002/0187184 | A1 | 12/2002 | Golomb et al. |
| 2002/0192157 | A1 | 12/2002 | Low et al. |
| 2003/0013686 | A1 | 1/2003 | Golomb et al. |
| 2003/0064965 | A1 | 4/2003 | Richter |
| 2003/0100514 | A1 | 5/2003 | Ahotupa et al. |
| 2003/0118637 | A1 | 6/2003 | Jordon et al. |
| 2003/0157179 | A1 | 8/2003 | Blum et al. |
| 2003/0225132 | A1 | 12/2003 | DiNinno et al. |
| 2004/0005345 | A1 | 1/2004 | Pauletti et al. |
| 2004/0147484 | A1 | 7/2004 | Boyd et al. |
| 2004/0175417 | A1 * | 9/2004 | Proffitt ............... A61K 31/7048 424/450 |
| 2004/0223971 | A1 | 11/2004 | Chang et al. |
| 2004/0241222 | A1 * | 12/2004 | Metselaar ............ A61K 9/1271 424/450 |
| 2004/0265391 | A1 | 12/2004 | Danenberg et al. |
| 2004/0266734 | A1 | 12/2004 | Danenberg et al. |
| 2005/0008633 | A1 | 1/2005 | Vanbever et al. |
| 2005/0118249 | A1 * | 6/2005 | Webb ................. A61K 9/1271 424/450 |
| 2005/0260256 | A1 * | 11/2005 | Hill .................... A61K 9/1277 424/450 |
| 2006/0222694 | A1 * | 10/2006 | Oh .................... A61K 9/127 424/450 |
| 2006/0239925 | A1 | 10/2006 | Wada et al. |
| 2007/0014845 | A1 | 1/2007 | Zhang et al. |
| 2007/0148196 | A1 | 6/2007 | Haas et al. |
| 2007/0298093 | A1 | 12/2007 | Konur et al. |
| 2008/0044464 | A1 * | 2/2008 | Tardi ................... A61K 9/127 424/450 |
| 2008/0187901 | A1 * | 8/2008 | Doorschodt ........ A01N 1/0226 435/1.2 |
| 2009/0238876 | A1 * | 9/2009 | Danenberg ............ A61K 31/00 424/489 |
| 2011/0002977 | A1 | 1/2011 | Chunlei et al. |
| 2011/0002982 | A1 | 1/2011 | Tardi et al. |
| 2011/0104052 | A1 | 5/2011 | Barnett et al. |
| 2011/0274625 | A1 | 11/2011 | Redelmeier et al. |
| 2012/0034296 | A1 * | 2/2012 | Epstein-Barash ...... A61K 31/02 424/450 |
| 2013/0041311 | A1 * | 2/2013 | Kohane ................ A61K 9/0009 604/22 |
| 2013/0048565 | A1 | 2/2013 | Fiering et al. |
| 2013/0122081 | A1 | 5/2013 | Hong et al. |
| 2019/0030168 | A1 * | 1/2019 | Gay ..................... A61K 47/36 |
| 2019/0167701 | A1 * | 6/2019 | Poras ................... A61P 27/02 |

FOREIGN PATENT DOCUMENTS

| | | |
|---|---|---|
| DE | 196 37 890 A1 | 3/1998 |
| EP | 0 339 237 | 11/1989 |
| EP | 0185756 | 8/1990 |
| EP | 0 459 318 | 12/1991 |
| JP | 61-502452 | 10/1986 |
| JP | H07-53593 | 2/1995 |
| JP | 10-265383 | 10/1998 |
| JP | 2001-515853 | 9/2001 |
| JP | 2007-515278 | 6/2007 |
| JP | 6176548 | 7/2017 |
| WO | WO 88/00289 | 1/1988 |
| WO | WO 93/09790 | 5/1993 |
| WO | WO 96/20698 | 7/1996 |
| WO | WO 97/16170 | 5/1997 |
| WO | WO 97/33552 | 9/1997 |
| WO | WO 97/43437 | 11/1997 |
| WO | WO 98/31359 | 7/1998 |
| WO | WO 99/17740 | 4/1999 |
| WO | WO 99/38998 | 8/1999 |
| WO | WO 99/40787 | 8/1999 |
| WO | WO 00/03677 | 1/2000 |
| WO | WO 00/21540 | 4/2000 |
| WO | WO 00/34293 | 6/2000 |
| WO | WO 00/56866 | 9/2000 |
| WO | WO 00/64516 | 11/2000 |
| WO | WO 00/69412 | 11/2000 |
| WO | WO 00/69503 | 11/2000 |
| WO | WO 01/05374 | 1/2001 |
| WO | WO 01/74337 | 10/2001 |
| WO | WO 02/083096 A1 | 10/2002 |
| WO | WO 02/096927 | 12/2002 |
| WO | WO 03/020243 | 3/2003 |
| WO | WO 03/075741 | 9/2003 |
| WO | WO 03/086351 | 10/2003 |
| WO | WO 03/086354 | 10/2003 |
| WO | WO 03/088950 | 10/2003 |
| WO | WO 03/089568 | 10/2003 |
| WO | WO 03/097696 | 11/2003 |
| WO | WO 2004/073610 | 9/2004 |
| WO | WO 2004/082626 | 9/2004 |
| WO | WO 2005/002545 | 1/2005 |
| WO | WO 2005/044175 | 5/2005 |
| WO | WO 2006/087722 A1 | 8/2006 |
| WO | WO 2006/126208 | 11/2006 |
| WO | WO 2010/107990 | 9/2010 |
| WO | WO 2010/143193 | 12/2010 |
| WO | WO 2011/144745 | 11/2011 |
| WO | WO 2012/080369 | 6/2012 |

OTHER PUBLICATIONS

European Patent Office, Communication pursuant to Article 94(3) EPC, App. No. 04756133.7-1219, 4 pages, dated Jan. 22, 2008.
European Patent Office, Communication pursuant to Article 94(3) EPC, App. No.04785964.0-1219, 5 pages, dated Jan. 22, 2008.

(56) References Cited

OTHER PUBLICATIONS

European Search Report and Written Opinion for related EP application 06795155.8-2112 dated Sep. 14, 2009.
International Search Report and Written Opinion dated Dec. 15, 2004 for related application PCT/US2004/020487.
International Search Report and Written Opinion dated Dec. 23, 2005 for related application PCT/US2004/020536.
International Search Report and Written Opinion dated Jul. 29, 2008 for corresponding application PCT/IB06/02028.
Afergan et al., "Delivery of Serotonin to the Brain by Monocytes Following Phagocytosis of Liposomes," Journal of Controlled Release 132 pp. 84-90 (2008).
Aikawa, Masanori, "Vascular Biology of the Acute Coronary Syndromes," Cardiovascular Division. Department of Medicine, Brigham and Women's Hospital, Harvard Medical School, Experimental Medicine, vol. 20, No. 3, 2002, p. 434-442.
Allaire, et al., "Endothelial Cell Injury in Cardiovascular Surgery: The Intimal Hyperplastic Response," *Ann. Thorac. Surg.*, 63(2):582-91 (1997).
Anderson, et al., "A review of randomized trials comparing coronary angioplasty and bypass grafting," *Curr-Opin-Cardiol.*, 11(6):583-90 (1996).
Arefieva, et al., "Monocyte Integrin Expression and Monocyte-Platelet Complex Formation in Humans with Coronary Restenosis," *Clin. Exp. Pharm. Physio.*, 28:804-8 (2001).
Beers and Berkow, "The Merck Manual of Diagnosis and Therapy," Merck Research Laboratories, Whitehouse Stations, 1999.
Bellah, et al., "Idiopathic arterial calcification of infancy: Prenatal and postnatal effects of therapy in an infant," *The Journal of Pediatrics*, 121(6):930-3 (1992).
Benford, et al., "Farnesol and Geranylgeraniol Prevent Activation of Caspases by Aminobisphosphonates: Biochemical Evidence for Two Distinct Pharmacological Classes of Bisphosphonate Drugs," *Mol. Pharmacol.*, 56:131-140 (1999).
Bergh, et al., "Liposome-mediated macrophage depletion: an experimental approach to study the role of testicular macrophages in the rat," *J. Endocrinol.*, 136:407-13 (1993).
Biewenga, et al., "Macrophage depletion in the rat after intraperitoneal administration of liposome-encapsulated clodronate: depletion kinetics and accelerated repopulation of peritoneal and omental macrophages by administration of Freund's adjuvant," *Cell. Tissue Res.*, 280:189-196 (1995).
Bohm, et al., "Exogenous Hepatitis B Surface Antigen Particles Processed by Dendritic Cells or Macrophages Prime Murine MHC Class I-Restricted Cytotoxic T Lymphocytes In Vivo," *J. Immunol.*, 155:3313-21 (1995).
Bolli et al., Evidence That Late Preconditioning Against Myocardial Stunning in Conscious Rabbits is Triggered by the Generation of Nitric Oxide, Circulation Research 1997; 81:42-52, American Heart Association, Inc.
Boras, et al., "Diabetes and Coronary Heart Disease," *Endocrinology and Metabolic Diseases*, 31-4:199-208 (2002).
Buiting, et al., "Liposomes as antigen carriers and adjuvants in vivo," *Res. Immunol.*, 143:541-8 (1992).
Cendejas-Santana et al., "Progesterone Crystallization from a Solvent: a New Procedure," Mat. Res. Innovat 6: 252-255 (2002).
Cipollone et al., "Elevated Circulating Levels of Monocyte Chemoattractant Protein-1 in Patients with Restenosis After Coronary Angioplasty", 2001, Arterioscler Thromb Vase Biol, vol. 21, pp. 327-334.
Cohen, et al., "Synthesis and Preclinical Pharmacology of 2-(2-Aminopyrimidinio) Ethylidene-1,1-Bisphosphonic Acid Betaine (ISA-13-1)—A Novel Bisphosphonate," *Pharma. Res.*, 16(9):1399-1406 (1999).
Daoud, et al., "The effect of ethane-1-hydroxy-1, 1-diphosphonate (EHDP) on necrosis of atherosclerotic lesions," *Atherosclerosis*, 67:41-8 (1987).
Donbrow, "Microcapsules and Nanoparticles in Medicine and Pharmacy," CRC Press, Boca Raton, FL, pp. 1-347 (1992).

Epstein-Barash, Hila, Immunomodulation by Liposomal Delivery Systems for Vascular Healing, Thesis Submitted to the Senate of the Hebrew University, 194 pages (Nov. 2006).
Fisher et al., "Alendronate Mechanism of Action: Geranylgeraniol, An Intermediate in the Mevalonate Pathway, Prevents Inhibition of Osteoclast Formation, Bone Resorption, and Kinase Activation In Vitro," Proc. Natl. Acad. Sci. USA, vol. 96, pp. 133-138 (Jan. 1999).
Fleisch, "Bisphosphonates in Bone Disease," Parthenon Publishing Group Inc., pp. 184-207 (1997).
Flora, L., "Comparative Antiinflammatory and Bone Protective Effects of Two Diphosphonates in Adjuvant Arthritis," Arthritis Rheum. 22(4): 340-6 (Apr. 1979).
Definition of opsonization by the Free Dictionary, retrieved from http://www.thefreedictionary.com/opsonization on Nov. 28, 2014, pp. 1-2.
Frith, et al., "The Molecular Mechanism of Action of the Antiresorptive and Antiinflammatory Drug Clodronate: Evidence for the Formation In Vivo of a Metabolite That Inhibits Bone Resorption and Causes Osteoclast and Macrophage Apoptosis," *Arth. Rheum.*, 44:2201-2210 (2001).
Gaytan, et al., "In vivo manipulation (depletion versus activation) of testicular macrophages: central and local effects," *J. Endocrinol.*, 150:57-65 (1996).
Gennaro, "Parenteral Preparations," Remington: The Science and Practice of Pharmacy, 20th Edition, Ch. 41, pp. 780-806, 2000.
Goldmann, et al., "Risk Stratification in Acute Coronary Syndrome," *Herz*, vol. 26, Supplement 1, pp. S24-S29, Background Section, Mar. 2001.
Gottsauner-Wolf, et al., "Influence of local delivery of the protein tyrosine kinase receptor inhibitor tyrphostin-47 on smooth-muscle cell proliferation in a rat carotid balloon-injury model," *Am. Heart J.*, 19:329-34 (1997).
Hamon, et al., "Restenosis after coronary angioplasty," *Eur. Heart J.*, 16:33-48 (1995).
Hirota et al., "Endocytosis of Particle Formulations by Macrophages and Its Application to Clinical Treatment," InTech: Chapter 16-Molecular Regulation of Endocytosis, 2012, 16 pages.
Hyvönen et al, "Influence of Dichloromethylene Bisphosphonate on the In Vitro Phagocytosis of Hydroxyapatite Particles by Rat Peritoneal Exudate Cells: An Electron Microscopic and Chemiluminescence Study," Annals of the Rheumatic Diseases 51; 203-209 (1992).
Jalowy et al., "AT1 Receptor Blockade in Experimental Myocardial Ischemia/Reperfusion," Basic Research in Cardiology vol. 93: Suppl. 2, 85-91 (1998).
Kramsch, et al., "The Effect of Agents Interfering with Soft Tissue Calcification and Cell Proliferation on Calcific Fibrous-Fatty Plaques in Rabbits," *Circulation Res.*, 42(4):562-570 (1978).
Kunitomo et al., "Experimental Induction of Athero Sclerosis in guinea-Pigs Fed a Cholesterol Vitamin D-2-Rich Diet," 1983.
Langer, R., "New Methods of Drug Delivery," *Science*, 249:1527-33 (1990).
Laurent, et al., "The arterial wall: a new pharmacological and therapeutic target," *Fundam. Clin. Pharmacol.*, 10:243-57 (1996).
Leclerc, et al., "Drug Prevention of Restenosis After Angioplasty: An Update," Elsevier Science, pp. 722-724 (1995).
Leenaars, et al., "Increased adjuvant efficacy in stimulation of antibody responses after macrophage elimination in vivo," *Immunol.*, 90:337-43 (1997).
Lefkovits, et al., "Pharmacological Approaches for the Prevention of Restenosis After Percutaneous Coronary Intervention," *Progress in Cardiovascular Disease*, 40(2):141-58 (1997).
Lehenkari, et al., "Further Insight into Mechanism of Action of Clodronate: Inhibition of Mitochondrial ADP/ATP Translocase by a Nonhydrolyzable, Adenine-Containing Metabolite," *Mol. Pharmacol.*, 62:1255-1262 (2002).
Li et al., Kinetics of Tumor Necrosis Factor $\alpha$ in plasma and the cardioprotective effect of a monoclonal antibody to tumor necrosis factor $\alpha$ in acute myocardial infarction, 1999, American Heart Journal, vol. 137, No. 6, pp. 1145-1152.
Lodge-Patch, Ian, "The Ageing of Cardiac Infarcts, and it's Influence on Cardiac Rupture," Br Heart J. 13(1): 37-42 (Jan. 1951).

(56) References Cited

OTHER PUBLICATIONS

Luckman, et al., "Nitrogen-Containing Bisphosphonates Inhibit the Mevalonate Pathway and Prevent Post-Translational Prenylation of GTP-Binding Proteins, Including Ras," Journal of Bone and Mineral Research 13:581-589 (Apr. 1998).
Maekawa et al., Prognostic Significance of Peripheral Monocytosis: After Reperfused Acute Myocardial Infarction: A Possible Role for Left Ventricular Remodeling, 2002, J Am Coll Cardiol, vol. 39, No. 2, pp. 241-246.
Mak, et al., "Clinical Trials to Prevent Restenosis after Perculaneous Coronary Revascularization," The NY Academy of Sciences, pp. 256-288 (1994).
Makkar, et al., "Prevention of Restenosis by Local Drug Delivery," *J. Cardiovasc. Pharmacol. Therapeut.*, 1(2):177-88 (1996).
Makkonen, et al., "Contrasting effects of alendronate and clodronate on RAW 264 macrophages: the role of a bisphosphonate metabolite," *Eur. J. Pharm. Sci.*, 8:109-118 (1999).
Makkonen, et al., "Different Effects of Three Bisphosphonates on Nitric Oxide Production by Raw 264 Macrophage-Like Cells in Vitro," *J. Pharmacol. Exp. Ther.*, 277:1097-1102 (1996).
Makkonen, et al., "The Effect of Free Gallium & Gallium in Liposomes on Cytokine and Nitric Oxide Secretion from Macrophage-Like Cells in Vitro," Inflamm Res 44:523-528 (1995).
Martin et al., "Bisphosphonates—Mechanisms of Action," Australian Prescriber vol. 23, No. 6 pp. 130-132 (2000).
Maximilian et al., "Effect of EHDP on Calcium Accumulation and Technetium-99m Pyrophosphate Uptake in Experimental Myocardial Infarction", Circulation, vol. 64, No. 5, pp. 1012-1017 (1981).
Mateos-Cáreres et al., "Prior Aspirin use in Unstable Angina Patients with Modified Plasma Inflammatory Markers and Endothelial Nitric Oxide Synthase in Neutrophils," European Journal of Clinical Investigation, vol. 32, pp. 895-900 (2002).
Matsuo, Hiroya—Abstract—"Bone Loss Induced by GnRHa Treatment in Women," Nippon Rinsho, vol. 61, No. 2, p. 314-318, 2003.
Matthews et al., "Comparison of the Response of Primary Human Peripheral Blood Mononuclear Phagocytes from Different Donors to Challenge with Model Polyethylene Particles of Known Size and Dose," Biomaterials 21, pp. 2033-2044 (2000).
McLaren, et al., "Vascular Endothelial Growth Factor is Produced by Peritoneal Fluid Macrophages in Endometriosis and is Regulated by Ovarian Steriods," J. Clin. Invest., vol. 98 (2): 482-489 (Jul. 1996).
Monkkonen, et al., "The Cellular Uptake and Metabolism of Clodronate in RAW 264 Macrophages," *Pharm. Res.*, 18:1550-1555 (2001).
Monkkonen, et al., "Effects of clodronate and pamidronate on splenic and hepatic phagocytic cells of mice," *Pharmacol. Toxicol.*, 68:284-286 (1991).
Monkkonen et al., "The Effects of Liposome-Encapsulated and Free Clodronate on the Growth of Macrophage-Like Cells In Vitro: The Role of Calcium and Iron," Calcif. Tissue Int., 53:139-146 (1993).
Monkkonen, et al., "The effects of liposome surface charge and size on the intracellular delivery of clodronate and gallium in vitro," *Int. J. Pharm.*, 107:189-197 (1994).
Monkkonen, et al., "Effects of Tiludronate and Ibandronate on the Secretion of Proinflammatory Cytokines and Nitric Oxide from Macrophages in Vitro," Life Sci., 62:PL95-102 (1998).
Monkkonen, et al., "Growth Inhibitions of Macrophage-Like and Other Cell Types by Liposome-Encapsulated, Calcium-Bound, and Free Bisphosphonates In Vitro," *J. Drug Targeting*, 2:299-308 (1994).
Monkkonen, et al., "Liposome-Mediated Delivery of Gallium to Macrophage-Like Cells in Vitro: Demonstration of a Transferrin-Independent Route for Intracellular Delivery of Metal Ions," *Pharm. Res.*, 10(8):1130-1135 (1993).
Monkkonen et al., "Studies on Liposome Formulations for Intra-Articullar Delivery of Clodronate," J. Controlled Release, 35:145-154 (1995).
Moorman, et al., "Percutaneous Transluminal Coronary Angioplasty (PTCA): Long-term Outcome and Aeromedical Implications," *Aviation, Space and Environmental Medicine*, 67(10):990-6 (1996).

Mukae et al., "Phagocytosis of Particulate Air Pollutants by Human Alveolar Macrophages Stimulates the Bone Marrow," Am J. Physiol Lung Cell Mol Physiol 279: L924-L931, Jun. 9, 2000.
Mullane et al., "Role of Leukocytes in Acute Myocardial Infarction in Anesthetized Dogs: Relationship to Myocardial Salvage by AntiInflammatory Drugs," The Journal of Pharmacology and Experimental Therapeutics, vol. 228, No. 2, pp. 510-522 (1984).
Nandi et al., "Synergistic Effect of PEG-400 and Cyclodextrin to Enhance Solubility of Progesterone," AAPS PharmSciTech. 2003; 4(1): article 1, 7 pages.
Paspaliaris, et al., "Clodronate Inhibits Contraction and Prevents the Action of L-Type Calcium Channel Antagonists in Vascular Smooth Muscle," *J. Bone Min. Res.*, 6(8):835-841 (1991).
Patashnik et al., "Preparation and Evaluation of Chitosan Microspheres Containing Bisphosphonates", J. Drug Targeting, 4:371-380 (1997).
Pennanen, et al., "Effect of Liposomal and Free Bisphosphonates on the IL-1ß, IL-6 and TNF-α Secretion from RAW 264 Cells In Vitro," *Pharma. Res.*, 12(6):916-922 (1995).
Perugini et al., "Long-Term Release of Clodronate from Biodegradable Microspheres," AAPS PharmSciTech. 2001; 2(3): article 10, 11 pages.
Remington's Pharmaceutical Sciences, A.R. Gennaro, ed. Mack Publishing Co. (18th ed. 1990) p. 993.
Presentation by Inventor Yoram Richter from Examiner Interview submitted Aug. 21, 2008 in prosecution of related U.S. Appl. No. 10/871,488.
Rogers, et al., "Monocyte Recruitment and Neointimal Hyperplasia in Rabbits," Arteriosclerosis, Thrombosis, and Vascular Biology, vol. 16, No. 10, pp. 1312-1318 (Oct. 1996).
Rubin, et al., "Cellular and Molecular Mechanisms of Radiation Inhibition of Restenosis. Part I: Role of the Macrophage and Platelet-Derived Growth Factor," *Int. J. Radiation Oncology Biol. Phys.*, 40:929-41 (1998).
Saito et al., "An Investigation of the Stabilization and Regression of Coronary Lesions by Lipid-Lowering Therapy," 66th Annual Scientific Meeting of the Japanese Circulation Society Conference, Japanese Circulation Journal, vol. 10, No. 2, Oct. 2002, p. 233-236.
Sansoni et al., Abstract—"Inhibition of Antigen-Presenting Cell Function by Alendronate In Vitro," J-Bone-Miner-Res. Nov. 1995; 10(11): 1719-25.
Schachter, et al., "Peritoneal Macrophage Depletion by Liposomal Bisphosphonate Inhibits Implant Growth in a Rat Model—a Novel Approach to Endometriosis Immunotherapy," European Journal of Obstetrics & Gynecology and Reproductive Biology 123, S58 (2005).
Schroeter et al., "Phagocytic Response in Photochemically Induced Infarction of Rat Cerebral Cortex," Stroke, 28:382-386 (1997).
Schwartz, "The vessel wall reaction in restenosis," *Semin. Intervent. Cardiol.*, 2:83-8 (1997).
Selander, et al., "Characteristics of the Clodronate-Induced Apoptosis in Osteoclasts and Macrophages," *Mol. Pharmacol.*, 50:1127-1138 (1996).
Shioi, et al., "ß-Glycerophosphate Accelerates Calcification in Cultured Bovine Vascular Smooth Muscle Cells," *Arteriosclerosis, Thrombosis and Vascular Biology*, 15(11):2003-9 (1995).
Siiteri et al., "Immunologic & Endocrine Interrelationships in Pregnancy," Biology of Reproduction 26, 1-14 (1982).
Szebeni, Janos, "The Interactions of Liposomes with the Complement System," *Critical Reviews in Therapeutic Drug Carrier Systems*, 15(1):57-88 (1998).
Takayama, et al. "Treatment of Severe Postmenopausal Endometriosis with an Aromatase Inhibitor," Fertility and Sterility, vol. 69, No. 4; 709-713 (Apr. 1998).
Tashiro, et al., "Monocyte-Related Cytokines in Acute Myocardial Infarction," American Heart Journal, 130: 446-452 (1995).
Taubes et al., "Does Inflammation Cut to the Heart of the Matter?", Science, vol. 296, No. 5566 pp. 242-245 (2002).
Thepen, et al., "Alveolar macrophage elimination in vivo is associated with an increase in pulmonary immune response in mice," *J. Exp. Med.*, 170:499-509 (1989).

(56) References Cited

OTHER PUBLICATIONS

Toyras, et al., "Inhibition of mevalonate pathway is involved in alendronate-induced cell growth inhibition, but not in cytokine secretion from macrophages in vitro," *Eur. J. Pharm. Sci.*, 19:223-230 (2003).
"Unnerving Truth About Diabetic Neuropathy," Diabetes Facts, Diabetes Research, http://www.allaboutdiabetes.net/unnerving-truth-about-diabetic-neuropathy/, Nov. 30, 2008, 5 pages.
Van Lent, et al., "In Vivo Role of Phagocytic Synovial Lining Cells in Onset of Experimental Arthritis," American Journal of Pathology, vol. 143:, No. 4, pp. 1226-1237(Oct. 1993).
Van Offel et al., "Influence of Cyclic Intravenous Pamidronate on Proinflammatory Monocytic Cytokine Profiles and Bone Density in Rheumatoid Arthritis Treated with Low Dose Prednisolone and Methotrexate," Clinical and Experimental Rheumatology 19: 13-20 (2001).
Van Rooijen, et al., "Apoptosis of macrophages induced by liposome-mediated intracellular delivery of clodronate and propamidine," *J. Immunol. Methods*, 193:93-9 (1996).
Van Rooijen et al., "Elimination of Phagocytic Cells in the Spleen after Intravenous Injection of Liposome-Encapsulated Dichloromethylene Diphosphonate: An Enzyme-Histochemical Study" Cell and Tissue Research (1984) 238: pp. 355-358.
Van Rooijen, et al., "In vitro and in vivo elimination of macrophage tumor cells using liposome-encapsulated dichloromethylene diphosphonate," *Virchows Arch. B (Cell Pathol.)*, 54:241-245 (1988).
Van Rooijen, et al., "In vivo elimination of macrophages in spleen and liver, using liposome encapsulated drugs: methods and applications," *Liposomes as drug carriers: Trends and progress*, Ed. G. Gregoriadis, John Wiley and Sons, Chichester, U.K. (chapter 9), pp. 131-143 (1988).
Van Rooijen, N., "Liposomes as an in vivo tool to study and manipulate macrophage function: Introduction 41$^{st}$ Forum in Immunology," *Res. Immunol.*, 143:177-178 (1992).
Van Rooijen, et al., "Liposome mediated depletion of macrophages: mechanism of action, preparation of liposomes and applications," *J. Immunol. Methods*, 174:83-93 (1994).
Van Rooijen, N., "Macrophages as accessory cells in the in vivo humoral immune response: from processing of particulate antigens to regulation by suppression," *Semin. Immunol.*, 4:237-245 (1992).
Van Rooijen, et al., "Macrophage subset repopulation in the spleen: differential kinetics after liposome-mediated elimination," *J. Leuk. Biol.*, 45:97-104 (1989).
Van Rooijen, et al., "The Macrophage as Target or Obstacle in Liposome-Based Targeting Strategies," International Journal of Pharmaceutics 162 pp. 45-50 (1998).
Van Rooijen, et al., "Transient suppression of macrophage functions by liposome-encapsulated drugs," *Trends in Biotechnology*, 15(5):178-185 (1997).
Wagner, et al., "Contrasting Effects of Ethane-1-Hydroxy-1,1-Diphosphonate (EHDP) on the Regression of two types of Dietary-Induced Atherosclerosis," *Atherosclerosis*, 27:419-35 (1977).
Walsh, et al., "Molecular strategies to inhibit restenosis: modulation of the vascular myocyte phenotype," *Semin. Intervent. Cardiol.*, 1:173-9 (1996).
Waller, et al., "Coronary Artery and Saphenous Vein Graft Remodeling: A Review of Histologic Findings after Various Interventional Procedure—Part VI," *Clin. Cardiol.*, 20:153-60 (1997).
Webb, et al., "Inhibition of Bioprosthetic Heart Valve Calcification with Aminodiphosphonate Covalently Bound to Residual Aldehyde Groups," *Ann. Thorac. Surg.*, 46:309-16 (1988).
Witte, Ow, "Delayed and Remote Effects of Focal Cortical Infarctions: Secondary Damage and Reactive Plasticity," Adv Neurol, 73: 207-27 (1997).
www.clodronateliposomes.com, copyright (c) 1984-2003, download date Sep. 4, 2003.
Ylitalo, "Bisphosphonates and Atherosclerosis," General Pharmacology, 35: 287-296 (2002).
Ylitalo, et al., "Effects of liposome-encapsulated bisphosphonates on acetylated LDL metabolism, lipid accumulation and viability of phagocyting cells," *Life Sciences*, vol. 62, No. 5, pp. 413-422 (1998).
YourDictionary, scientific definition of "heart attack", accessed Jun. 2, 2011 from http://science.yourdictionary.com/heart-attack.
Yue et al., "In Vivo Myocardial Protection From Ischemia/ Reperfusion Injury by the Peroxisome Proliferator—Activated Receptor- γ Agonist Rosiglitazone," Circulation, 104:2588-2594 (2001).
Zhao et al., "Myocardial Apoptosis and Ischemic Preconditioning," Cardiovascular Research 55 pp. 438-455 (2002).
Office Actions and Responses of co-related U.S. Appl. No. 11/816,245, granted now U.S. Pat. No. 8,257,742: • Notice of Allowance dated Jul. 6, 2012; • Petition Decision dated Jun. 26, 2012; • Petition to Withdraw from Issue, Amendment to Specification, Supplemental Application Data Sheet, and Request for Continued Examination (RCE) dated Jun. 25, 2012; • Post-Allowance Communication dated Jun. 14, 2012; • Notice of Allowance and Examiner Initiated Interview Summary dated May 10, 2012; • Amendment and Response to Non-Final Office Action dated Feb. 24, 2012; • Non-Final Rejection dated Nov. 28, 2011; • Amendment and Response to Final Rejection and Request for Continued Examination (RCE) dated Aug. 16, 2011; • Final Rejection dated May 16, 2011; • Amendment and Response to Non-Final Office Action dated Apr. 13, 2011; and •Non-Final Rejection dated Jan. 20, 2011.
Office Actions and Responses of co-related U.S. Appl. No. 10/607,623: • Non-Final Rejection dated Feb. 27, 2018; • Amendment and Response to Final Rejection with Request for Continued Examination dated Sep. 21, 2017; • Applicant Initiated Interview Summary dated Aug. 17, 2017; • Final Rejection dated Jun. 22, 2017; • Amendment and Response to non-Final Rejection with extension of time and Affidavit dated Mar. 1, 2017; • Non-Final Rejection dated Oct. 3, 2016; • Amendment and Response to Final Rejection with Extension of Time and Request for Continued Examination dated Jul. 22, 2016; • Advisory Action dated Jul. 11, 2016; and • Final Rejection dated Mar. 3, 2016.
Office Actions and Responses of co-related U.S. Appl. No. 10/607,623: • Amendment and Response to Non-Final Rejection and extension of time dated Nov. 11, 2015; • Non-Final Rejection dated Jul. 15, 2015; • Amendment and Response to Final Rejection with Request for Continued Examination (RCE) and extension of time dated May 20, 2014; • Pre-Brief Appeal Conference Decision dated Jan. 27, 2014; • Pre-Brief Conference Request and Notice of Appeal dated Aug. 19, 2013; • Final Rejection dated May 22, 2013; • Amendment and Response to Final Rejection with Request for Continued Examination (RCE) dated Aug. 7, 2012; • Final Rejection dated May 10, 2012; • Amendment and Response to Non-Final Rejection dated Jan. 30, 2012; • Non-Final Rejection dated Oct. 31, 2011; • Amendment and Response to Non-Final Rejection dated Jul. 14, 2011; • Non-Final Rejection dated Apr. 15, 2011; • Amendment and Response to Non-Final Rejection dated Dec. 8, 2010; • Notice regarding Non-Compliant or Non-Response Amendment dated Dec. 3, 2010; • Informal or Non-Responsive Amendment to Non-Final Rejection and extension of time dated Nov. 29, 2010; Non-Final Rejection dated Aug. 25, 2010; Amendment and Response to Final Rejection with Request for Continued Examination (RCE) and extension of time dated Jun. 30, 2010; • Pre-Brief Appeal Conference Decision dated Jun. 1, 2010; • Pre-Brief Conference Request and Notice of Appeal dated May 3, 2010 Final Rejection dated Feb. 4, 2010; • Examiner Interview Summary dated Nov. 16, 2009; • Amendment and Response to Non-Final Rejection with extension of time dated Nov. 10, 2009; • Non-Final Rejection dated Jun. 11, 2009; • Amendment and Response to Final Rejection with Request for Continued Examination (RCE) dated May 1, 2009; • Final Rejection dated Feb. 9, 2009; • Examiner Interview Summary dated Jul. 31, 2008; • Amendment and Response to Non-Final Rejection with extension of time dated Jul. 28, 2008; • Examiner Interview Summary dated Jul. 8, 2008; • Non-Final Rejection dated Apr. 3, 2008; • Amendment and Response to Final Rejection with Request for Continued Examination (RCE) and extension of time dated Jan. 7, 2008; • Non-Final Rejection dated Feb. 8, 2007; Response to Election/Restriction Requirement dated Jul. 26, 2006; • and Requirement for Restriction/Election dated Jun. 28, 2006.

(56) References Cited

OTHER PUBLICATIONS

Office Actions and Responses of co-related U.S. Appl. No. 10/871,488: • Applicant Initiated Interview Summary dated Nov. 1, 2016; • Notice of Allowance dated Jul. 13, 2016; • Examiner Initiated interview Summary dated Jul. 13, 2016; • Terminal Disclaimer Approval dated Jul. 7, 2016; • Terminal Disclaimer dated Jul. 7, 2016; • Amendment and Response to Non-Final Rejection dated Jun. 28, 2016; • Non-Final Rejection dated Mar. 31, 2016; • Amendment and Response to Final Rejection with Request for Continued Examination dated Feb. 25, 2016; • Advisory Action dated Feb. 4, 2016; • Response to Final Rejection dated Jan. 25, 2016; • Supplemental Amendment after Final Rejection dated Jan. 25, 2016; • Examiner Initiated Interview Summary dated Dec. 30, 2015; • Applicant Initiated Interview Summary dated Dec. 21, 2015; • Final Rejection dated Nov. 25, 2015; • Amendment and Response to Non-Final Rejection dated Nov. 10, 2015; • Non-Final Rejection dated Aug. 11, 2015; • Amendment and Response to Final Rejection with Request for Continued Examination (RCE) dated Jul. 15, 2015; • Applicant Initiated Interview Summary dated Jun. 23, 2015; • Final Rejection dated Apr. 17, 2015; • Amendment and Response to Non-Final Rejection with extension of time dated Apr. 3, 2015; • Non-Final Rejection dated Dec. 3, 2014; • Amendment and Response to Final Rejection with Request for Continued Examination (RCE) dated May 13, 2014; • Applicant Initiated Interview Summary dated Apr. 15, 2014; • Final Rejection dated Feb. 20, 2014; • Amendment and Response to Non-Final Rejection dated Dec. 16, 2013; • Non-Final Rejection dated Sep. 24, 2013; • Amendment and Response to Final Rejection with Request for Continued Examination (RCE) dated Feb. 9, 2012; • Applicant Initiated Interview Summary dated Dec. 8, 2011; • Final Rejection dated Nov. 10, 2011; • Amendment and Response to Non-Final Rejection with extension of time dated Aug. 24, 2011; • Non-Final Rejection dated Mar. 4, 2011; • Amendment and Response to Final Rejection with Request for Continued Examination (RCE) dated Dec. 22, 2009; • Final Rejection dated Oct. 29, 2009; • Amendment and Response to Non-Final Rejection with extension of time dated Jul. 13, 2009; • Non-Final Rejection dated Apr. 16, 2009; • Supplemental Response/ Amendment to Non-Final Rejection and extension of time dated Jan. 26, 2009; • Non-Final Rejection dated Sep. 25, 2008; • Amendment and Response to Final Rejection with Affidavits dated Aug. 21, 2008; • Examiner Interview Summary dated Jul. 3, 2008; • Final Rjection dated May 21, 2008; • Amendment and Response to Non-Final Rejection dated Feb. 25, 2008; • and Non-Final Rejection dated Nov. 26, 2007.

Office Actions and Responses of co-related U.S. Appl. No. 11/190,787: • Notice of Abandonment dated May 31, 2012; • Non-Final Rejection dated Nov. 17, 2011; • Amendment and Response to Final Rejection with Request for Continued Examination (RCE) dated Sep. 9, 2011; • Final Rejection dated Jun. 10, 2011; • Amendment and Response to Non-Final Rejection dated Jun. 1, 2010; • Non-Final Rejection dated Mar. 3, 2010; • Examiner Interview Summary dated Nov. 17, 2009; • Amendment and Response to Non-Final Rejection with extension of time dated Nov. 10, 2009; • Non-Final Rejection dated Jun. 11, 2009; • Amendment and Response to Non-Final Rejection with extension of time dated Feb. 25, 2009; • Non-Final Rejection dated Oct. 29, 2008; • Response to Election/ Restriction Requirement dated Aug. 29, 2008; • Notice regarding Non-Compliant or Non-Responsive Amendment dated Aug. 26, 2008; • Informal or Non-Responsive Amendment dated Aug. 21, 2008; • and Requirement for Restriction/Election dated Jul. 29, 2008.

Office Actions and Responses of co-related U.S. Appl. No. 15/336,395: • Notice of Allowance dated Aug. 3, 2017; • Amendment and Response to Non-Final Rejection dated Jul. 6, 2017; • Terminal Disclaimer Approval dated Jul. 6, 2017; • Terminal Disclaimer dated Jul. 6, 2017; • Non-Final Rejection dated Apr. 6, 2017; • and Preliminary Amendment dated Nov. 2, 2016.

Office Actions and response of co-related U.S. Appl. No. 13/804,707: • Response to Amendment under Rule 312 dated Mar. 9, 2018; • Amendment after Notice of Allowance (Rule 312) dated Feb. 26, 2018; • Notice of Allowance dated Feb. 16, 2018; • Notice of Allowance and Examiner Initiated Interview Summary dated Feb. 9, 2018; • Supplemental Amendment and Response dated Aug. 18, 2017; • Amendment and Response to Final Rejection with Request for Continued Examination and Affidavit dated Jun. 29, 2017; • Final Rejection dated Apr. 3, 2017; • Amendment and Response to Non-Final Rejection dated Mar. 20, 2017; • Applicant Initiated Interview Summary dated Feb. 28, 2017; • Non-Final Rejection dated Dec. 19, 2016; • Amendment and Response to Final Rejection with Request for Continued Examination and Affidavit dated Jul. 28, 2016; • Advisory Action, After Final Consideration Program Decision, and Examiner Initiated Interview Summary dated Jun. 1, 2016; • Notice of Appeal filed May 31, 2016; • Request for Examiner Interview dated May 18, 2016; • Advisory Action and After Final Consideration Program Decision dated May 12, 2016; • Response to Final Rejection with After Final Consideration Program Request dated May 2, 2016; • Final Rejection dated Feb. 29, 2016; • Amendment and Response to Non-Final Rejection dated Jan. 4, 2016; • and Non-Final Rejection dated Oct. 2, 2015.

International Search Report and Written Opinion from corresponding PCT Application No. PCT/IB2013/000951 dated Aug. 17, 2013, 11 pages.

Notice of Transmittal of the International Preliminary Report on Patentability dated May 6, 2015 for corresponding application No. PCT/IB2013/000951, 19 pages.

Athlin et al., "Phagocytosis of Yeast Cells by Monocytes: Effects of Fluorouracil, Doxorubicin and Mitomycin," European Journal of Surgical Oncology, 1987, vol. 13, No. 1, pp. 51-55.

Bogdan et al., "Taxol, a Microtubule-Stabilizing Antineoplastic Agent, Induces Expression of Tumor Necrosis Factor α and Interleukin-1 in Macrophages," Journal of Leukocyte Biology, vol. 52, Jul. 1992, pp. 119-121.

Cooper et al., "Rapamycin But Not FK506 Inhibits the Proliferation of Mononuclear Phagocytes Induced by Colony-Stimulating Factors," Transplantation, vol. 57, No. 3, Feb. 1994, pp. 433-439.

Danenberg et al., "Macrophage Depletion by Clodronate-Containing Liposomes Reduces Neointimal Formation After Balloon Injury in Rats and Rabbits," Circulation: Journal of the American Heart Association, Jul. 15, 2002, pp. 599-605.

Herrman, et al., "Pharmacological Approaches to the Prevention of Restenosis Following Angioplasty: The Search for the Holy Grail? (Part 1)," Drugs, 46(1): 18-52 (1993).

Iimuro et al., "Improvement of Survival Rate in Endotoxin Shock Model Rat By Administration of $GdCl_3$, Inhibitor of Liver Macrophage Phagocytosis," Digestive Organ and Immunology, No. 26, 1992, pp. 186-191.

Rosol et al., "Effects of Mithramycin on Calcium Metabolism and Bone in Dogs," Veterinary Pathology Online, vol. 29, pp. 223-229 (1992).

Suresh et al., "In Vitro Activation of Murine Bone Marrow-Derived Macrophages with Cisplatin and Mitomycin-C," Int. J. Immunopharmac., vol. 13, Nos. 2/3, pp. 189-195, 1991.

Takeshita et al., "Drug Action at a Cellular Level," Iryo, The Japanese Journal of the National Medical Services, Mar. 1979, vol. 33, No. 3, pp. 37-39.

Tanaka et al., "Cytotoxic Effects of Selenium on Mouse tsA640-transformed macrophages in vitro," Bulletin, Tottori University College of Medical Care Technology, 1992, No. 18, p. 13-20.

Viklicky et al., "SDZ-RAD Prevents Manifestation of Chronic Rejection in Rat Renal Allografts," Transplantation, 2000, vol. 69, No. 4, p. 497-502.

Epstein-Barash et al., "Physicochemical Parameters Affecting Liposomal Bisphosphonates Bioactivity for Restenosis Therapy: Internalization, Cell Inhibition, Activation of Cytokines and Complement, and Mechanism of Cell Death," Journal of Controlled Release 146 pp. 182-195 (2010).

Krivanek et al., "Interaction of the antimicrobial peptide gramicidin S with dimyristoyl-phosphatidylcholine bilayer membranes: a densitometry and sound velocimetry study", Biochimica et Biophysica Acta, 2001, N. 1510, pp. 452-463.

N.R. Kuznetsova, "Anticancer Liposomes with Diglycerol Conjugates of Methotrexate and Melphalan: Studying of Stability and

(56) References Cited

OTHER PUBLICATIONS

Interactions with the Components of Blood", extended Abstract of Cand. Chem. Sci. Dissertation, 2012.

Nakano, Koji, "Methods for Measuring Rigidity of Liposomes and Effect of Surface Modification of Submicron-sized Particles on Bio-interaction," Laboratory of Pharmaceutical Engineering, Gifu Pharmaceutical University, vol. 58, p. 19-28 (2009).

Chono, Sumio, "Development of Drug Delivery Systems for Targeting to Macrophages," The Pharmaceutical Society of Japan, Yakugaku Zasshi 127 (9) 1419-1430, 2007.

Ishida et al., "Interaction of Liposomes with Cell Membrane," Department of Pharmacokinetics and Biopharmaceutics, Institute of Health Biosciences, the University of Tokushima, Japan, vol. 32, No. 1, pp. 18-24-, 2007.

Office Actions and Responses of co-related U.S. Appl. No. 15/974,817: • Notice of Allowance and Examiner Initiated Interview Summary dated Dec. 5, 2018; • Terminal Disclaimer Approval dated Nov. 28, 2018; • Terminal Disclaimer filed Nov. 28, 2018; • Amendment and Response to Non-Final Rejection dated Nov. 6, 2018; • Non-Final Rejection dated Aug. 9, 2018; • and Preliminary Amendment dated May 21, 2018.

Office Actions and Responses of co-related U.S. Appl. No. 10/607,623: • Appeal Brief with Affidavit-Rule 131 dated Feb. 14, 2019; • Notice of Appeal dated Dec. 18, 2018; • Final Rejection dated Sep. 24, 2018; • and Amendment and Response to Non-Final Rejection dated May 21, 2018.

Russian Search Report for related application No. 2018110051 dated Nov. 6, 2019, 5 pages, with English translation.

Prenner EJ et al., "The interaction of the antimicrobial peptide gramicidin S with lipid bilayer model and biological membranes", Biochim et Biophysica Acta. 1462 (1999) 201-221.

Zarandona, Manuel et al., University of Pittsburgh Medical Center, "Case 422—Neuropathology Case: Sudden Onset of Polydipsia and Polyuria", Published Apr. 2005, available at https://path.upmc.edu/cases/case422.html; 2 pages, accessed Mar. 26, 2020.

University of Rochester Medical Center, "Osmolality (Blood)—Health Encyclopedia", available at https://www.urmc.rochester.edu/encyclopedia/content.aspx?contenttypeid=167&contentid=osmolality_blood; 5 pages, accessed Mar. 26, 2020.

Weill Medical College of Cornell University, "Serum Osmolality", available at http://www-users.med.cornell.edu/~spon/picu/calc/osmolal.htm; Published Jan. 7, 2000, Revised Oct. 3, 2000. 2 pages, accessed Mar. 26, 2020.

Al-Ahmady et al., "Lipid-Peptide Vesicle Nanoscale Hybrids for Triggered Drug Release by Mild Hyperthermia in vitro and in vivo," ACS Nano. Oct. 23, 2012; 6(10):9335-9346.

\* cited by examiner

LIPOSOME FORMULATION AND MANUFACTURE

This application is a continuation of U.S. patent application Ser. No. 15/974,817, filed May 9, 2018, which is a continuation of U.S. patent application Ser. No. 13/804,707, filed Mar. 14, 2013 and issued as U.S. Pat. No. 9,993,427 on Jun. 12, 2018, all of which are incorporated herein by reference in their entirety.

FIELD OF THE INVENTION

The present invention relates to a novel liposome formulation and a manufacturing process for the liposome formulation.

BACKGROUND OF THE INVENTION

Liposomes are known in the art to function as carriers to deliver therapeutic agents to targeted cells for treating a variety of medical conditions. In one application, liposomes may be formulated to encapsulate a pharmaceutical agent that can be phagocytized selectively by macrophages. Once phagocytized, the liposome releases the agent intracellularly, inhibiting inflammatory functions of the macrophages, among other effects.

The art describes several methods for preparing such liposomes (see, e.g., Mönkkönen, J. et al., 1994, J. Drug Target, 2:299-308; Mönkkönen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993; 54(1-3):35-43). In one such method, liposomes are formed into stacks of liquid crystalline bilayers that are hydrated into hydrated lipid sheets, which detach during agitation and self-close to form large, multilamellar vesicles (MLV) known as thin lipid film hydration technique. Once these particles are formed, the size of the particle is dependent on the method used in the next steps of the process, for example, sonic energy (sonication) or mechanical energy (extrusion). Sonication typically produces small, unilamellar vesicles (SUV) and requires bath and/or probe tip sonicators. Alternatively, lipid extrusion which forces a lipid suspension through a series of polycarbonate filter—typically 0.8, 0.4, 0.2 and 0.1 μm membranes—at high pressure (up to 500 psi), produces particles having a diameter near the pore size of the filter used. These methods are limited to small-batch productions, primarily used for research purposes. Moreover, the high pressure extrusion techniques are associated with high operating costs and time. Thus, there remains a need in the art for a method of liposome production useful for commercial scale manufacture which is reproducible and addresses issues including quality control, stability, scalability and sterilization of liposome production.

In addition, liposomal formulations known in the art are not substantially uniform in size and shape which is a critical feature of a pharmaceutical composition to provide a sterile product and avoid potentially toxic side effects of aberrant large liposomes. Currently, it is difficult to manufacture a liposome formulation having a uniform size. The extrusion process of multilamellar vesicles through a series of filters including, for example, 100 nm polycarbonate filters does not consistently produce a formulation having substantially uniform population of liposomes having a 100 nm size. Indeed, depending on the physical characteristics of the liposomes, such as compressibility and/or stability, the mean vesicle diameter for extruded vesicles may vary considerably depending on the type and size of filters used. Thus, there is a need for a method of manufacture capable of producing liposomes substantially uniform in size and shape.

Moreover, many physical characteristics of the liposome formulation affect the cellular response to the liposome and impact the effectiveness of the liposome as a pharmaceutical composition. The physical characteristics of the liposome formulation are influenced in many respects by the manufacturing process. However, the art does not address how the liposomal properties can be controlled in the formulation process to manipulate manufacturing efficiency and liposome stability. Thus, there is a need for a large-scale manufacturing process that is cost effective, yet can control the characteristics of the liposome formulation to produce liposomes that are substantially uniform and suitable for clinical use.

SUMMARY OF THE INVENTION

The present invention describes novel liposomes encapsulating therapeutic agents. The invention also relates to liposomal formulations having a high degree of size uniformity which results in minimizing side effects and increasing confidence in sterilization processes. The invention also describes an efficient and cost-effective manufacturing process, for production of liposomes under low pressure extrusion conditions. Liposomes formulated by this process have desirable characteristics and efficacious therapeutic properties.

The liposome formulation is characterized by liposomes having desirable composition and physical characteristics. The liposome comprises lipid ingredients encapsulating a therapeutic agent. According to one aspect of the present invention, the lipid ingredients comprise diastearoylphosphatidylcholine (DSPC), diastearoylphosphatidylglycerol (DSPG) and cholesterol, preferably in a 3:1:2 molar ratio (DSPC:DSPG:chol).

The liposome is composed of a lipid ingredient and the therapeutic agent, having a ratio of the mass of the therapeutic agent to that of the lipid ingredient, called the drug:lipid ratio, of about 1:5 to 1:8 by weight, preferably 1:6 to 1:7. This drug:lipid ratio enhances stability and effectiveness, and also impacts drug release and liposome integrity. These and other structural characteristics impart unexpected benefits to the instant formulation.

The liposomes of the present invention are in the size range of 30-500 nm, preferably, 70-120 nm, 100-300 nm, 100-180 nm, and 70-150 nm, depending on the type of therapeutic agent and/or the carrier used. In one preferred embodiment, the liposomes may be 80±5 nm in size.

Other physical characteristics of the liposome composition also contribute significantly to its stability and effectiveness. For example, the conductivity of the liposome, which may affect selective uptake into phagocytic cells. In one embodiment, the conductivity is between 13.5-17.5 ms/cm. Similarly, the external and internal osmolality of the formulation affects stability and effectiveness. Preferably, the external osmolality is matched with that of the human body whereas the internal osmolality is sufficiently low to enhance stability of the formulation. In one embodiment of the invention, the internal osmolality is between 340-440 mO/kg. Another favorable parameter is the pH of the liposome and/or the liposome formulation. For example, an internal pH of about 6.9 for the liposomal formulation has a beneficial effect on long term stability as well as drug leakage rate and drug encapsulation capability.

The liposomes of the invention are relatively rigid compared to those in the art, as characterized by having liposomal membranes which are less compressible. Liposomes of the invention have compressibility less than 0.7 ml/g. Due to their greater rigidity, the liposomes of the present invention have improved stability and shelf-life.

The liposome formulation also has novel and useful characteristics. The liposome formulation of the present invention is comprised of liposomes which are substantially uniform in size and shape distribution, while being relatively rigid. The formulation has little size variation as from one liposome to another. The uniformity of the liposomes, as measured by the Poly Diversity Index ("PDI"), less than 0.075, preferably in the range of about 0.02-0.05, signifying a composition having high uniformity. Accordingly, the liposome formulation of the present invention advantageously reduces the incidence of adverse events associated with large liposomes, and allows sterile filtration to be performed efficiently.

Another aspect of the invention is a process for manufacturing a liposomal formulation. The manufacturing method includes the steps of (1) mixing a therapeutic agent with preselected lipids to form vesicles, (2) extruding the vesicles in a single-stage through a single-sized filter, and (3) ultrafiltration. Following ultrafiltration, the product may optionally be standardized to the desired final concentration. Because the extrusion of step 2 is performed as a single-stage extrusion under low pressure, the present method saves operating costs and time and increases yield over high pressure extrusions utilizing multiple stages. These manufacturing steps are adaptable for large-scale production.

In one embodiment of the manufacturing process, the formulation is prepared by (1) mixing a therapeutic agent with lipids comprising DSPC, DSPG and cholesterol in a molar ratio of about 3:1:2 to form vesicles such that the mass ratio of said therapeutic agent to lipid is in the range of about 1:5 to 1:8, (2) extruding the vesicles in a single-stage through a filter having a pore size about 100 nm, and (3) ultrafiltration.

Yet another aspect of this invention is a liposome formulation made in accordance with the manufacturing steps above. The formulation comprises a plurality of liposomes, composed of an amount of lipid ingredient encapsulating a therapeutic agent. For example, said lipid ingredient comprising DSPC, DSPG and cholesterol in a molar ratio of about 3:1:2, and the mass ratio of said therapeutic agent to lipid ingredient may be in the range of about 1:5 to 1:8. The formulation is manufactured by the following steps: (1) mixing a therapeutic agent with preselected lipids to form vesicles, (2) extruding the vesicles in a single stage through a single sized filter, and (3) ultrafiltration. Following ultrafiltration, the product may optionally be standardized to the desired final concentration. Preferable, the formulation made in accordance with this method has a PDI less than 0.075, more preferably in the range between 0.02 and 0.05. This process produces a liposome formulation of the having novel and useful features, including, for example, the 3:1:2 ratio of the lipid ingredient, the drug:lipid ratio, PDI, rigidity, pH, osmolality and conductivity.

DETAILED DESCRIPTION OF THE INVENTION

Figure 1:
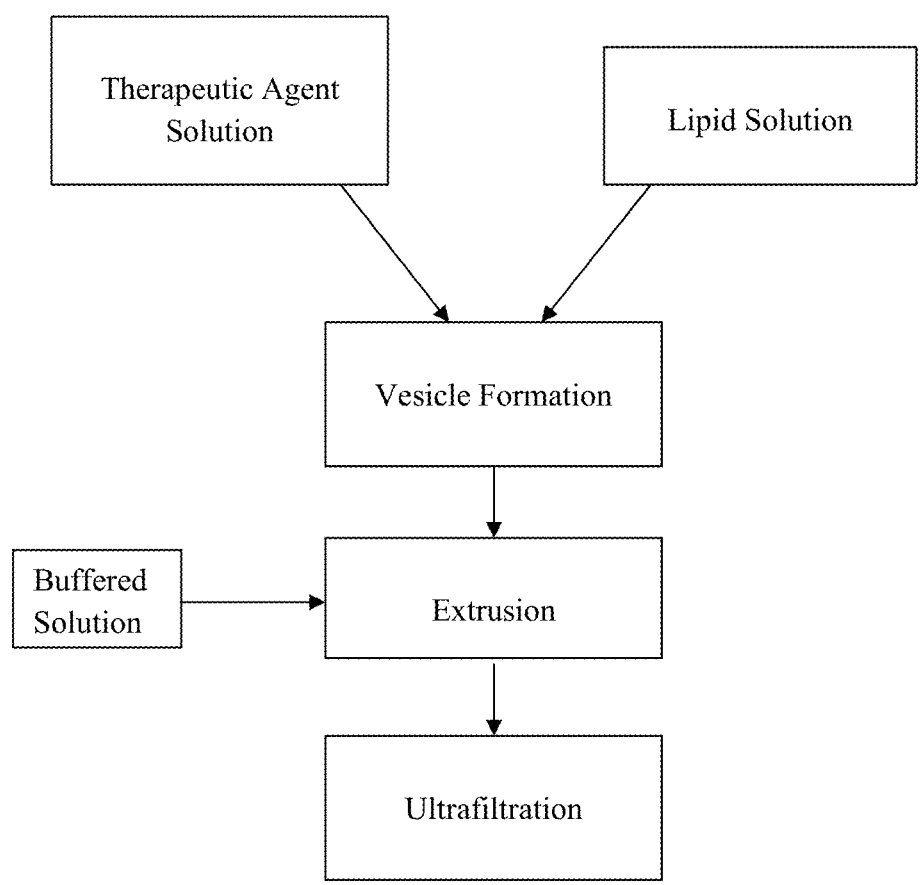
FIG. 1 is a flow chart of the manufacturing process of the liposomal formulation of the present invention.

The present invention relates to a novel liposome, formulation and a method of making same for use in the treatment of various diseases. The formulation comprises a plurality of liposomes encapsulating a therapeutic agent, or an "encapsulated agent." The physical characteristics of each liposome facilitates stability and effectiveness of the liposomal formulation. The formulation is characterized by liposomes which are substantially uniform in size and shape. Also, the invention describes an efficient and cost-effective manufacturing process for the liposome formulation, while meeting the needs of large-scale production. Further, the invention relates to a formulation having novel and useful properties produced by said manufacturing process.

A. Components of the Liposome

The present invention relates to novel and useful forms of a liposome. Different liposome ingredients may be used to form the liposome of the invention. Preferably, the lipid ingredient is non-toxic biocompatible lipids, such as, for example, lipids prepared from phosphatidyl-choline, phosphoglycerol, and/or cholesterol. In one embodiment of the present invention, the lipid ingredient comprises diastearoylphosphatidylcholine (DSPC), diastearoylphosphatidylglycerol (DSPG) and cholesterol, preferably in a molar ratio of about 3:1:2 (DSPC:DSPG:chol).

The lipid ingredient encapsulates a therapeutic agent, wherein both components have a preselected mass. As used herein, the "drug to lipid ratio" (or drug:lipid ratio) refers to the relative amounts of the drug to the lipid ingredient, by mass, that comprise the liposome and/or formulation. In one embodiment of the invention, the liposome has a drug:lipid ratio between about 1:5 and 1:8, preferably, between 1:6 and 1:7 by weight.

B. Physical Properties of Liposomes

Various physical parameters and characteristics of the liposomes may affect the uniformity, stability and effectiveness of the formulation. These physical characteristics include (1) osmolality (internal and external to the liposome), (2) conductivity (internal and external to the liposome), (3) drug to lipid ratio, (4) the pH (internal and external to the liposome), and (5) the type of lipids and drugs used in the composition.

Osmolality is the measure of the concentration of solutes of the liposomal formulation. As used herein, the term "osmolality" refers to the measure of solute concentration as defined by the number of solute molecules in milliosmoles (mO) of solute per kilogram of solvent (mO/kg). The internal osmolality is the concentration of solutes within the liposome, where the external osmolality is the concentration of solutes outside the liposome. In one embodiment of the invention, the liposome has a low internal liposomal osmolality. Internal osmolality can be adjusted by varying the amount of drug that is encapsulated within the liposome. The art describes liposomes that contain as much drug as possible, resulting in liposomes with high osmolality (high encapsulation ratio). However, the present invention discloses liposomes having a lower osmolality (or low encapsulation ratio) as compared to those in the art. The lower osmolality, i.e., between about 340-440 mO/kg, as disclosed herein improves the stability of the liposomes and the uniformity of the liposomes within the formulation. One way to achieve a low internal osmolality is to decrease the amount of therapeutic agent encapsulated in the liposome formulation. Another way to lower internal osmolality, which does not require varying the drug:lipid ratio, utilizes a non-charged agent, such as certain polysaccharides or sugars known in the art.

The external osmolality is preferably isotonic to that of the body, especially for injectable formulations, to be isotonic to that of the body. As such, the external osmolality is preferably relatively constant. The internal and external osmolality of the invention results in a product having high stability, low drug leakage rate and proper drug encapsulation capability of the liposome.

As used herein, the term "conductivity" refers to the ability of the liposome to conduct electricity based on the ionic content of the solution. Conductivity is related to the ionic content of the liposome and affects stability, drug leakage rate and drug encapsulation capability of the liposome formulation. The conductivity of the liposome is in the range of about 13.5-17.5 ms/cm. In one embodiment of the invention, the encapsulated drug agent is charged. It is noted that a charged drug has a one-to-one correlation between conductivity and the osmolality of the liposome. Therefore, altering the amount of a charged agent to be encapsulated proportionally affect both properties. In an alternative embodiment, a neutral (non-charged) drug agent may be used. Where a neutral agent such as a polysaccharide, for example, is used to adjust conductivity, osmolality is independent from the concentration of the drug and thus can be controlled independently from the concentration of the agent.

Another novel aspect of the liposomes of the instant invention is the relative rigidity of the composition, i.e., the stability of the liposome in different environmental and internal body conditions, and its susceptibility to break apart. Liposome rigidity is a measure of the strength of the liposome membrane and its ability to resist shear force and pressure, which can improve the shelf-life of the liposomes. The rigidity of liposomes is inversely related to its compressibility. Liposomes having low compressibility have greater rigidity. One exemplary method of determining liposome rigidity is through ultrasound velocimetry and densitometry. Methods of determining liposome rigidity are known in the art, and are detailed in, for example, Cavalcanti, Leide P., et al., "Compressibility study of quaternary phospholipid blend monolayers", *Colloids and Surfaces B: Biointerfaces* 85(2011) 153-160; and Hianik, Tibor, et al., "Specific volume and compressibility of bilayer lipid membranes with incorporated Na, K-ATPase", *General Physiology and Biophysics* 30(2011) 145-153, the entire contents of which are incorporated herein by reference.

The liposome has a pH for both the solvent external to the liposome (the external pH) and the internal encapsulated portion of the liposome (the internal pH). The pH affects the stability, drug leakage rate from the liposome and drug encapsulation capability of the liposome formulation. One embodiment of the formulation has an internal pH in the range of about 6.8-7.0. The internal 6.8-7.0 pH is beneficial to the stability of the formulation. The pH of the solvent for the therapeutic agent may be maintained, among other means, by continuously titrating the solution to remain in the 6.8-7.0 pH range or held at a particular pH such as, for example, about pH 6.9 as the therapeutic agent is dissolved using a known buffer. The internal pH of the liposome may be different from the external pH of the liposome. A different pH can be achieved by varying the pH of the solutions that make up the internal and external environments of the liposome.

C. The Formulation

The liposomal formulation of the present invention comprises a plurality of liposomes having the characteristics described above and being substantially uniform in size and shape, that is, having little size variation as from one liposome to another liposome. Uniformity of the formulation is measured by its Poly Dispersity Index (PDI). PDI is measured on a non-linear scale of 0 to 1, where a value of 0 is a perfectly uniform preparation while a composition having a PDI of 1 has high diversity (non-uniformity). The formulation of the present invention has a PDI less than 0.075, preferably in the range between 0.02-0.05. PDI values may be calculated as discussed in Zetasizer nano series user manual, 2003, Malvern Instruments, pp. 5.5-5.6 and Kazuba M., Nano Series and HPPS Training Manual Chapter 1, 2003, Malvern Instruments, pp. 9, the contents of which are incorporated by reference. Indeed, the PDI of the current formulation is close to that of sizing standards where PDI is less than 0.02. Formulations previously known in the art have substantially different uniformity than that of the present invention, with a PDI typically around 0.3. As PDI is a non-linear scale, the PDI of the present invention is substantially distinct than that of formulations in the art. Indeed, the low PDI of the present invention advantageously avoids the toxic effects associated with large liposomes, and produces a formulation more suitable for filter sterilization.

The formulation of the present invention contains liposomes of increased rigidity and uniformity, improving its stability and shelf life. Further, it is contemplated that the formulations of the present invention are efficacious. Banai, Shmuel, et al., "Targeted anti-inflammatory systemic therapy for restenosis: The Biorest Liposomeal Alendronate with Stent sTudy (BLAST)—a double blind, randomized clinical trial", Am Heart J. (2013) 165(2): 234-40.

Liposomes of the instant formulation are specifically sized so as to be taken-up by the macrophage and monocytes. The liposomes may be in the size range of 30-500 nm. However, depending on the type of agent and/or the carrier used, the ranges include, but are not limited to, 70-120 nm, 100-500 nm, 100-300 nm, 100-180 nm, and 80-120 nm. These ranges, however, are examples and other particular sizes suitable for up-take via phagocytosis will be recognized in the art without departing from the spirit or scope of the invention. In one preferred embodiment, the size of the liposome within the formulation is about 80±5 nm.

A variety of therapeutic agents may be encapsulated by the liposomes of the invention. Once the liposome is phagocytosed, the therapeutic agent is a substance that can decrease or inhibit the activity of and/or eliminate the amount of phagocytic cells in a patient. The therapeutic agent may be any chemical entity, including large or small molecules, a mixture of chemical compounds, inorganic or organic compound, a biological macromolecules such as proteins, carbohydrates, peptides, antibodies and nucleic acids. Therapeutic agents can be natural products derived from known organisms or synthetic compounds.

One type of therapeutic agent is useful in this invention are bisphosphonates. Bisphosphonates (formerly called diphosphonates) are compounds characterized by two C—P bonds. If the two bonds are located on the same carbon atom (P—C—P) they are termed geminal bisphosphonates. The bisphosphonates are analogs of the endogenous inorganic pyrophosphate which is involved in the regulation of bone formation and resorption. The bisphosphonates may at times form polymeric chains. Being highly hydrophilic and negatively charged, bisphosphonates in their free form are almost entirely incapable of crossing cellular membranes.

The term bisphosphonate as used herein, denotes both geminal and non-geminal bisphosphonates. A preferred agent, a bisphosphonate, has the following formula (I):

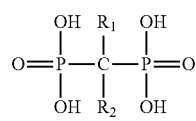

wherein $R_1$ is H, OH or a halogen atom; and $R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino where the amino may be a primary, secondary or tertiary; —NHY where Y is hydrogen, $C_3$-$C_8$ cycloalkyl, aryl or heteroaryl; or $R_2$ is —SZ where Z is chlorosubstituted phenyl or pyridinyl.

One example of a bisphosphonate agent is alendronate, having the following formula (II):

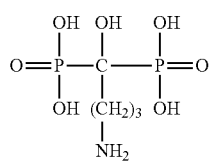

Many bisphosphonates have activities similar to that of alendronate and are useful as therapeutic agents for the invention. Such bisphosphonates may be selected on the basis of their ability to mimic the biological activity of alendronate. This includes, for example: in vitro activity in inhibiting activity of phagocytic cells, e.g. macrophages and fibroblasts once inside such cell; inhibition of secretion of IL-1 and/or IL-6 and/or TNF-α from macrophages; and in vivo activity, e.g., the ability of the tested formulations to deplete or disable blood monocytes in an animal model or in humans or to treat myocardial infarction and reduce the zone of infarct.

Bisphosphonates applicable in the present invention, include, but are not limited to, clodronate, tiludronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); and 1-hydroxy-2-(imidazo[1,2-a]pyridin-3-yl)ethane-1,1-diphosphonic acid, e.g., YM 529.

In certain embodiments, such as, e.g., sodium alendronate encapsulated in DSPC, DSPG and cholesterol, a 1:5.7 drug:lipid mass ratio—equal to approximately a 1:3 molar ratio for sodium alendronate—may be used. Where clodronate disodium, another therapeutic agent, is encapsulated in the same lipid ingredient, an approximately 1:5.4 mass ratio—equates to a 1:3 molar ratio—may be used. Other therapeutic agents that inhibit or deplete phagocytic cells by eliminating, retarding the proliferation and/or down regulating the activity of the phagocytic cells may be encapsulated in the present invention. Specific therapeutic agents include any agent that is cytotoxic or cytostatic, including but not limited to, for example, gallium, gold, silica, 5-fluorouracil, cisplatin, alkylating agents, mithramycin and paclitaxol. In any of the above therapeutic agents, the drug:lipid ratio of the liposome is between about 1:5 and 1:8, preferably, between 1:6 and 1:7 by weight.

In one embodiment, the formulation contains the encapsulated therapeutic agent that may enter a cell via phagocytosis and selectively target macrophage and monocytes without affecting other non-phagocytic cells. Because macrophages and monocytes, in their normal state, are recruited to a cellularly damaged area and promote inflammation beyond that caused by the disease or condition alone, monocyte/macrophage inhibition and/or depletion may attenuate the underlying damaged area. Once inside the phagocytic cells, the agent is released and inhibits, inactivates, disables, kills and/or depletes the monocytes and/or macrophages for treatment of various conditions involving a phagocytic immune response, such as, for example, ischemic reperfusion injury or inflammatory injury, such as, for example, myocardial infarction, reduction in the final zone of infarct and improvement of cardiac repair and outcome following acute myocardial infarction. The liposomes of the formulation have specific characteristics, including size, charge, pH, conductivity and osmolality that allow uptake primarily via phagocytosis.

After being taken-up by the monocytes/macrophages, the agent has a sustained inhibitory activity on the monocytes/macrophages. This sustained activity is sufficient to modulate the monocyte/macrophage's inflammatory action. Thus, prolonged release of the agent is not required in order to sustain inhibition. Accordingly, the method of treating certain diseases by inhibiting monocytes/macrophages, such as, for example, by the use of an encapsulated agent, is preferably a systemic therapy, in that the formulation targets the circulating monocytes and macrophages. Depending on the type of therapeutic agent encapsulated, the phagocytic cells may respond differently. For example, alendronate encapsulated liposomes cause apoptosis, while clodronate encapsulated liposomes cause necrosis. Non-phagocytic cells are relatively incapable of taking up the formulation due to the particular physiochemical properties of the liposomal formulation.

Furthermore, the liposomes of the present invention not only retain the therapeutic agent for a sufficient time so that the agent is not released in the body fluids, but also efficiently discharge the agent within the target cell. The liposomes of the present invention deliver an effective amount of the agent to the targeted cells. The term "effective amount" denotes an amount of the formulation which is effective in achieving the desired therapeutic result, e.g., treatment of endometriosis, restenosis, ischemia reperfusion injury (IM), myocardial infarction or other related conditions. For example, the decrease in number and/or activity of activated macrophages and monocytes reduces the zone of infarct and/or improves remodeling when the injury relates to myocardial damage. The effective amount may also depend on a number of factors including, but not limited to: weight and gender of the treated individual; the mode of administration of the formulation (namely whether it is administered systemically or directly to the site); the therapeutic regime (e.g., whether the formulation is administered once daily, several times a day, once every few days, or in a single dose); clinical indicators of inflammation; clinical factors influencing the rate of development of the underlying condition to be treated, smoking, hypercholesterolemia, pro-inflammatory states, renal diseases; and on the dosage form of the composition. The successful delivery and administration of the liposomal formulation depend from its stability and effectiveness. The number of therapeutic agent molecules encapsulated in each liposome (payload), vesicle size, and level of free un-encapsulated material are the important parameters that determine the therapeutic index of the product.

D. Dosage and Administration

The liposomal formulations may be administered by any route which effectively transport the liposomes to the appropriate or desirable site of action. Preferred modes of administration include intravenous (IV) and intra-arterial (IA) (particularly suitable for on-line administration). Other suitable modes of administration include intramuscular (IM), subcutaneous (SC), and intraperitonal (IP). Such administration may be bolus injections or infusions. Another mode of administration may be by perivascular delivery. The formulation may be administered directly or after dilution. Combinations of any of the above routes of administration may also be used in accordance with the invention. Any route of administration may be utilized provided that the particles are in contact with phagocytic cells (e.g., circulating monocytes or peritoneal macrophages).

Pharmaceutical compositions for use in accordance with the present invention may be formulated using one or more physiologically acceptable carriers comprising excipients and auxiliaries known in the art, which facilitate processing of the active ingredients into preparations which, can be used pharmaceutically.

Dosage amount and interval may be adjusted individually to provide plasma levels of the formulation sufficient to induce or suppress the biological effect (minimal effective concentration, "MEC"). The MEC will vary for each preparation, but can be determined from in vitro data. Dosages necessary to achieve the MEC will depend on individual characteristics and route of administration. Detection assays can be used to determine plasma concentrations.

Depending on the severity and responsiveness of the condition to be treated, dosing can be a single or a plurality of administrations, with course of treatment lasting from several hours to several weeks or until treatment is effected. The frequency of administration may vary depending on the condition and the severity. In one embodiment, the formulation may be administered periodically. The dosage may be formulated to any amount or volume as required for the desired treatment. For example, either a 1 µg or a 10 µg dose may be administered to patients undergoing an intravascular procedure, e.g., stent implantation, in order to prevent the incidence and severity of in-stent late loss. As a further example, the dosage may be at least 100 µg. In this regard, the formulation may be administered as a single dose, multiple doses and/or continuously, e.g., by continuous infusion(s) over a period of time. For example, dosages may be administered in accordance with those described in Banai, Am Heart J. (2013), supra.

E. Liposome Manufacturing Process

Another aspect of the invention relates to a process of making the liposome and liposomal formulation for commercial manufacture of the product. This manufacturing method permits the manipulation of the physical characteristics described above, as well as control of certain process parameters, including the water to solvent ratio, solvent composition and solvent ratios, vesicle preparation temperature, vesicle preparation shear rate, extrusion temperature, extrusion pressure, and extrusion membrane size and membrane type.

The preparation of the liposome formulation includes the steps of (1) mixing a therapeutic agent and preselected lipids to form vesicles, (2) extruding the vesicles in a single stage through a single-sized filter, and (3) ultrafiltration. Single-stage filter extrusions as that phrase is used means that the extrusion step uses a single pore-size filtration step. It may include multiple passes through the single sized filter but avoids the need for multiple and/or sequential passes through different sized filters as is known in the prior art, e.g., passes through 1.0, 0.8, 0.6, 0.4 and 0.2 µm membranes sequentially. Following ultrafiltration, the product may be standardized to the desired final concentration. Because the extrusion of step (2) is performed as a single-stage extrusion under low pressure, the present method saves operating costs and time and increases yield over high pressure extrusions utilizing multiple stages. FIG. 1 illustrates the steps of the manufacturing process.

The first step comprises mixing a therapeutic agent and preselected lipid ingredients in a solution to form vesicles. In many cases, the therapeutic agent and lipid ingredient will be solubilized into a therapeutic agent solution and lipid ingredient solution before mixing the two. In this embodiment, the therapeutic agent solution will have certain physical characteristics, including a pH, osmolality and conductivity. The therapeutic agent solution comprises the internal environment of the liposome formulation. As such, the pH, conductivity, osmolality of the therapeutic agent solution influences the internal pH, conductivity, osmolality of the liposomal formulation. The internal liposomal osmolality is preferably in the range between 340-440 mO/kg while the external liposomal osmolality is between 270-340 mO/kg. The pH of the solution is intended to keep the therapeutic agent solution in the intended pH range. Thus, if an acidic therapeutic agent is used, e.g., a bisphosphonate, a basic pH solution may be used to maintain the pH of the solution between 6.8 to 7.0. For example, a therapeutic agent solution may be prepared from sodium alendronate dissolved in a NaOH solution, with the resulting pH of the alendronate solution about 6.8 and conductivity about 18.0 ms/cm. The solution may optionally be heated during the process. In an alternate embodiment, sodium clodronate or alendronate monohydrate may be used. The solution may be heated to a temperature that facilitates solubilization of the bisphosphonate in the basic solvent, ranging from 55° to 75° C., such as, for example, 70° C. Depending on the quantity of therapeutic agent and other excipients dissolved, the solution may have an osmolality—which becomes the internal osmolality—in the range of 340-400 mO/kg. Also depending on the amount of therapeutic agents and excipients, the solution may have a conductivity—which becomes the internal conductivity—in the range of 14.0-21.0 ms/cm. The internal pH, osmolality, conductivity are factors in the stability and effectiveness of the liposomal formulation. In one embodiment, the therapeutic agent solution concentration may be in the range of 20-120 g/L during step (1) of the manufacturing process. The therapeutic agent solution may be prepared apart from and/or prior to the manufacturing process discussed herein.

The lipid ingredients may be in the form of a solution containing the desired starting amount of the lipid ingredient in a volume of one or more lipid solvent. Any suitable lipid ingredient and lipid solvent may be used. For example, the lipid ingredients may comprise DSPC, DSPG and cholesterol in a 3:1:2 molar ratio, respectively, prior to liposome formation. The resultant liposome formed according to this combination of lipids may also have a 3:1:2 molar ratio of DSPC, DSPG and cholesterol. Further, the lipid solvent may, for example, comprise t-butanol, ethanol and water in a 77/77/6 v/v/v ratio, respectively. Other lipid solvents usable to formulate the liposomes of the invention include chloroform or methanol. The lipid ingredients are dissolved in the lipid solvent. The lipid solvent may be heated to a temperature that facilitates solubilization of the lipid ingredients, ranging from 55° to 75° C., such as, for example 70° C. to generate the lipid solution. The concentration of the dissolved lipid solution may be in the range of 50-350 g/L. The lipid solution may be prepared apart from and/or prior to the manufacturing process discussed herein.

The mixing of the therapeutic agent solution and the lipid solution forms multi-lamellar vesicles (MLV). The drug:lipid ratio may be controlled by varying the amount of lipid solution or therapeutic agent solution. Mildly heating the two solutions may optionally be used to aid in mixing the solutions together. This process results in efficient encapsulation of the therapeutic agent into multi-lamellar vesicles. In one example, the lipid solution may be added to a therapeutic agent solution at a 5.3 part lipid to 1 part therapeutic agent. This ratio of lipid to drug (by weight) increases the stability of the liposome formulation without significant compromise to delivery. Indeed, this process permits the drug:lipid ratio to be varied in the range of 1:4 to 1:8 by weight, preferably in the range of 1:5 to 1:6. Further, the solvent concentration may be adjusted prior to the extrusion step without compromising the integrity of the liposome.

The next step in the method of manufacturing the formulation comprises extruding the vesicles in a single-stage through a single-sized filter. Extrusion of the vesicles reduces the size of the multi-lamellar vesicles described above. The method uses a single-extrusion step and low pressure, which produces liposomes that are highly-uniform in size and shape. The extrusion process may involve the use of a microfluidizer or other conventional homogenizer. Homogenizers rely on shearing energy to fragment large liposomes into smaller ones. Homogenizers suitable for use herein include microfluidizers produced by a variety of manufacturers, for example, Microfluidics in Boston, Mass. The particle size distribution can be monitored by conventional laser beam particle size discrimination. Extrusion of liposomes through a polycarbonate membrane or an asymmetric ceramic membrane is an effective method for reducing liposome sizes to a relatively well defined size distribution. The extrusion temperature is preferably above the liposome's transient phase temperature to enable size reduction. For example, in the case of DSPG, DSPC and cholesterol, about 55° C. may be desirable. Other lipids may be used and their known transient phase temperature is a measure of the desired temperature for the extrusion step. Multiple passes may be required to achieve the desired vesicle size and homogeneity. Samples may be analyzed in real time to assess vesicle size as well as bacterial count during this step.

The extrusion step is performed in a one-stage low pressure extrusion process technique. In the extrusion process, the MLV are processed in one stage by extruding directly through one membrane while applying low pressure—rather than creating small unilamellar liposomes by multi-stage extrusions where larger liposomes are passed through successively smaller membranes by extruders under high pressure (as practiced in the prior art methods). In one embodiment, the one-stage extrusion process is carried out directly with a 0.1 µm pore size polycarbonate or ceramic membrane while applying low pressure of 60-90 psi to obtain liposomes 100 nm in size. Also, the process uses a lower pressure of 60-90 psi, in contrast to higher pressure (up to 500 psi) of high pressure extrusions.

By eliminating multiple membranes and extruding under low pressure, the process of the invention has a number of advantageous. First, the one-stage extrusion process has the advantage of performing the extrusion process in less time than in multi-stage extrusion processes. Further, eliminating the need for high-pressure extrusions advantageously saves the high cost associated with the high-pressure extrusion equipment. Low pressure extruders are significantly less costly. One example of a suitable extruder for the present invention is the LIPEX™ Extruder, available from Northern Lipids, Inc. Moreover, the materials used for low pressure extruders, e.g., compressed air, generally cost less than those for high pressure extruders, e.g., nitrogen. Further, the reduction of multi-stage extrusions to a single-stage extrusion corresponds to similar reduction in waste and higher yields.

The last step of the instant method comprises ultrafiltration of the extruded vesicles into a buffered solution. While the extrusion process produces liposomes that are uniform in size and shape, ultrafiltration involves applying pressure to the formulation through a membrane in order to separate the encapsulated liposomes from the unencapsulated therapeutic agent, solvents and lipids. This step is preferably carried out below the transient phase temperature of the lipids used in the formulation, for example below 45° C. in most cases. Different types of filtration membranes may be used during the ultrafiltration process. One embodiment of the ultrafiltration step uses a hollow fiber membrane, where the formulation is pushed through the open hollow cores of the fiber, and the micromolecules (i.e., solvent, unencapsulated bisphosphonates, lipids) are filtered through the outer membrane of the fiber while the relatively larger liposomes remain within the fiber. The ultrafiltration results in a formulation having greater than or equal to 96% encapsulated therapeutic agent.

The ultrafiltration step may further include a dialyzing step wherein the formulation is dialyzed against a volume of a buffered solution. One example of a buffered solution is a phosphate saline buffer (PBS), but any buffer containing a balance of positive and negative ions maintained at a physiological osmolality may be used. Other buffer additives are known in the art and may include, for example, sucrose, glycine, sodium succinate, and/or albumin. The buffered solution preferably reflects the external environment of the final formulation, so that the pH and conductivity of this solution may be carefully monitored. Preferably, the buffered solution is isotonic and non-toxic to cells. The buffered solution may be filtered to further reduce contaminants and may be prepared in advance of the manufacturing process.

The dialysis end point is marked by reaching the desired pH and conductivity of the formulation.

At the end of the ultrafiltration step, the formulation may optionally be filtered for sterilization, i.e., to maintain bioburden control. In one embodiment of the process, a sterilization filter is connected to a pressure vessel containing the liposome formulation. The sterilization filter is further connected to a sterile reception tank. Applying pressure to the liposomal formulation forces the formulation through the sterilization filter. Further, another sample may be taken for bacterial content during this step. The sterilization filter pore size may be in the range of 0.2 to 0.45 μm. Because the liposomes of the formulation are substantially uniform and large liposome are absent, sterilization filtration may be performed relatively free from complication.

Following manufacture, the formulation may be standardized. Final standardization produces a liposome formulation batch having a standard concentration. Standardization analyzes the yield, size, lipid composition, drug and free drug content and concentration of the product. The concentration analysis may be performed by a method known in the art, such as, e.g., HPLC, phosphate assay via spectrophotometer. Upon confirming the concentration of the ultrafiltrated product, a volume of the buffered solution is used to dilute the formulation to a standard concentration. Final standardization also involves sterile filtration of the liposome product. For example, an encapsulated bisphosphonate formulation following ultrafiltration may be diluted with the appropriate amount of the buffered solution to arrive at a final concentration. Similarly, the ultrafiltrated product may be separated into multiple batches to be used in different final concentrations by using different amounts of the buffered solution diluent in the different batches. A sample may be taken to determine the achieved concentration of the therapeutic agent.

This manufacturing process has the advantage that the physiological and chemical features of the liposome can be controlled, monitored and reproduced. For example, the internal pH of the liposome may be controlled by the composition of the solution in which the therapeutic agent is dissolved. The internal osmolality may also be similarly manipulated by varying the amount of therapeutic agent or, for example, depending on whether it is charged or a non-charged agent. The drug:lipid ratio may be managed by the selection of the lipid ingredients comprising the liposome or the amount of lipids added to the dissolved active agent. Increasing the amount of lipid ingredient decreases the drug:lipid ratio, and vice versa. A low drug:lipid ratio also lowers internal osmolality of the liposome formulation. The external pH and external osmolality of the composition is influenced in part by the composition of the buffered solution that contain the final product. Conductivity may be controlled by the nature of the therapeutic agent and other excipients encapsulated within the liposome. Other factors, including, but not limited to viscosity, excipient quality, sterility, compatibility with saline, infusion kits and syringes (for injectable preparations), and compatibility with processing equipment, are also independently controllable by the process of the invention.

In accordance with the above description, in one preferred embodiment of the manufacturing process, the formulation is prepared by (1) mixing a solution containing a therapeutic agent with a solution containing lipids comprising DSPC, DSPG and cholesterol in a molar ratio of about 3:1:2 to form vesicles such that the mass ratio of said therapeutic agent to lipid is in the range of about 1:5 to 1:8, (2) extruding the vesicles in a single stage through a filter having a pore size about 100 nm, and (3) ultrafiltrating.

Another aspect of this invention is a liposome formulation made in accordance with the manufacturing steps above wherein the formulation comprises DSPC, DSPG and cholesterol in a molar ratio of about 3:1:2, and the mass ratio of said therapeutic agent to lipid is in the range of about 1:5 to 1:8 and is manufactured by the following steps: (1) mixing a solution containing a therapeutic agent with a solution containing lipid ingredients to form vesicles, (2) extruding the vesicles in a single stage through a single sized filter, and (3) ultrafiltrating. Following ultrafiltration, the product may be standardized to the desired final concentration. The formulation made in accordance with this method has a PDI less than 0.075, preferably in the range between 0.02 and 0.05. This process produces a liposome formulation having novel and useful features as described above, including, for example, the 3:1:2 ratio of the lipid ingredient, a drug:lipid ratio between 1:5 to 1:8. Moreover, the individual liposomal characteristics, including, pH, osmolality, conductivity and rigidity, may be independently controlled as outlined above.

The following examples are intended to illustrate and exemplify the various aspects of carrying out the present invention and are not intended to limit the invention in any way. The invention herein is described, by way of example only, with reference to the accompanying drawings. With specific reference now to the drawings in detail, it is stressed that the particulars shown are by way of example and for purposes of illustrative discussion of the preferred embodiments of the present invention only, and are presented in the course of providing what is believed to be the most useful and readily understood description of the principles and conceptual aspects of the invention. The description should be considered with the drawings making apparent to those skilled in the art how the several forms of the invention may be embodied in practice.

Example 1—Liposome Formulation Batch Preparation

In accordance with the process described above, an example batch was prepared. Clearly the batch size may be varied, as desired for commercial production. In this example, a one liter batch of liposomal alendronate encapsulated in liposomes containing cholesterol, DSPC and DSPG, and dispersed in phosphate buffer saline solution was produced. Liposomal alendronate may be provided in two concentrations, for clinical convenience: 5 mg/ml and 0.5 mg/ml, as a sterile whitish, liposomal dispersion. These concentrations may be further formulated to obtain a desired amount of therapeutic agent in any specific volume. The lipid ingredients were composed of cholesterol, DSPC and DSPG. The dispersion also contained a phosphate buffer saline solution for pH control, infusion suitability and for the maintenance of isotonicity. At least 96% of the drug in the final product was encapsulated in the liposomes. For administration, the content of the vial (or part of it, as needed) was diluted with saline, and then administered as an infusion.

A batch formula that includes the amount and quality of the components used in the manufacturing process and their amounts on a per 1 liter batch basis is presented in Table 1 below.

TABLE 1

Liposomal Alendronate for IV Infusion, Batch Formula for 1 Liter

| Component | Amount | Quality |
|---|---|---|
| Alendronate Sodium trihydrate | 68-80.75 g | 100.5% |
| NaOH | 6.8-8.0 g | Extra pure |
| Cholesterol | 10 ± 0.2 g | ≥99% |
| DSPC | 30 ± 0.4 g | ≥99% |
| DSPG | 10 ± 0.2 g | ≥99% |
| Ethanol | 77 ± 1.1 ml | Absolute, extra pure |
| t-butanol | 77 ± 1.1 ml | For analysis |
| Water for injection | 850 ± 13 ml | USP |
|  | 6 ± 0.1 ml |  |
| PBS pH 7 | ~6000 ml |  |
| $Na_2HPO_4 \cdot 2H_2O$ | 13.86 g ± 1.5% | Extra pure |
| $NaH_2PO_4 \cdot 2H_2O$ | 6.54 g ± 1.5% | Extra pure |
| NaCl | 50.82 g ± 1.5% | Extra pure |
| Water For Injection | 6000 ml | USP |

The contents and quantitative composition of liposomal alendronate for IV infusion produced in the 1 liter batch of Table 1 are summarized in Table 2 below. It is noted that in this batch, the molar ratio of DSPC:DSPG:cholesterol was 3:1:2. Also, the drug:lipid ratio was calculated to be about 1:5.7±1.5 w:w.

TABLE 2

Composition of Liposomal Alendronate for IV Infusion

| | | Composition | |
|---|---|---|---|
| | Component | 0.5 mg/ml | 5 mg/ml |
| Drug substance | Sodium Alendronate trihydrate | 0.5 + 0.05 mg/ml = 0.0015 mmol/ml | 5.0 + 0.2 mg/ml = 0.015 mmol/ml |
| Liposomal lipids | Cholesterol | 0.6 + 0.1 mg/ml = 0.0015 mmol/ml | 5.2 + 0.8 mg/ml = 0.013 mmol/ml |
| | DSPC (1,2-Distearoyl-sn-glycero-3-phosphocholine) | 1.7 + 0.3 mg/ml = 0.0022 mmol/ml | 15.65 + 2.35 mg/ml = 0.020 mmol/ml |
| | DSPG (1,2-Distearoyl-sn-glycero-3-phospho-rac-glycerol) | 0.6 + 0.1 mg/ml = 0.0007 mmol/ml | 5.2 + 0.8 mg/ml = 0.006 mmol/ml |
| Buffer solution (pH 7) | $NaH_2PO_4 \cdot 2H_2O$ | 1.09 mg/ml | 1.09 mg/ml |
| | $Na_2HPO_4 \cdot 2H_2O$ | 2.31 mg/ml | 2.31 mg/ml |
| | NaCl | 8.47 mg/ml | 8.47 mg/ml |
| | Water for injection (WFI) | ~1 ml | ~1 ml |

A liposomal alendronate formulation for IV infusion actually produced by the novel manufacturing process described herein is presented in Table 3 below.

TABLE 3

Specifications for 5 mg/ml Dosage Form

| Tests | Specification |
|---|---|
| Appearance | Whitish dispersion |
| Identification | Conforms |
| Alendronate Assay (HPLC) | 5.0 ± 0.2 mg/mL |
| Alendronate Encapsulation | >96% |
| DSPC Assay (HPLC) | 13.3-18.0 mg/mL |
| DSPG Assay (HPLC) | 4.4-6.0 mg/mL |
| Cholesterol Assay (HPLC) | 4.4-6.0 mg/mL |

TABLE 3-continued

Specifications for 5 mg/ml Dosage Form

| Tests | Specification |
|---|---|
| Drug:Lipid ratio (w:w) including Cholesterol | 1:5.3 ± 1.0 |
| Vesicle Size | Mean particle diameter 80 ± 5 nm |
| pH | 6.7-7.3 |
| Ethanol | <0.5% |
| t-Butanol | <0.5% |
| Osmolality | 270-340 mO/kg |
| Sterility | Sterile |
| Pyrogens | Pass |

Figure 2:
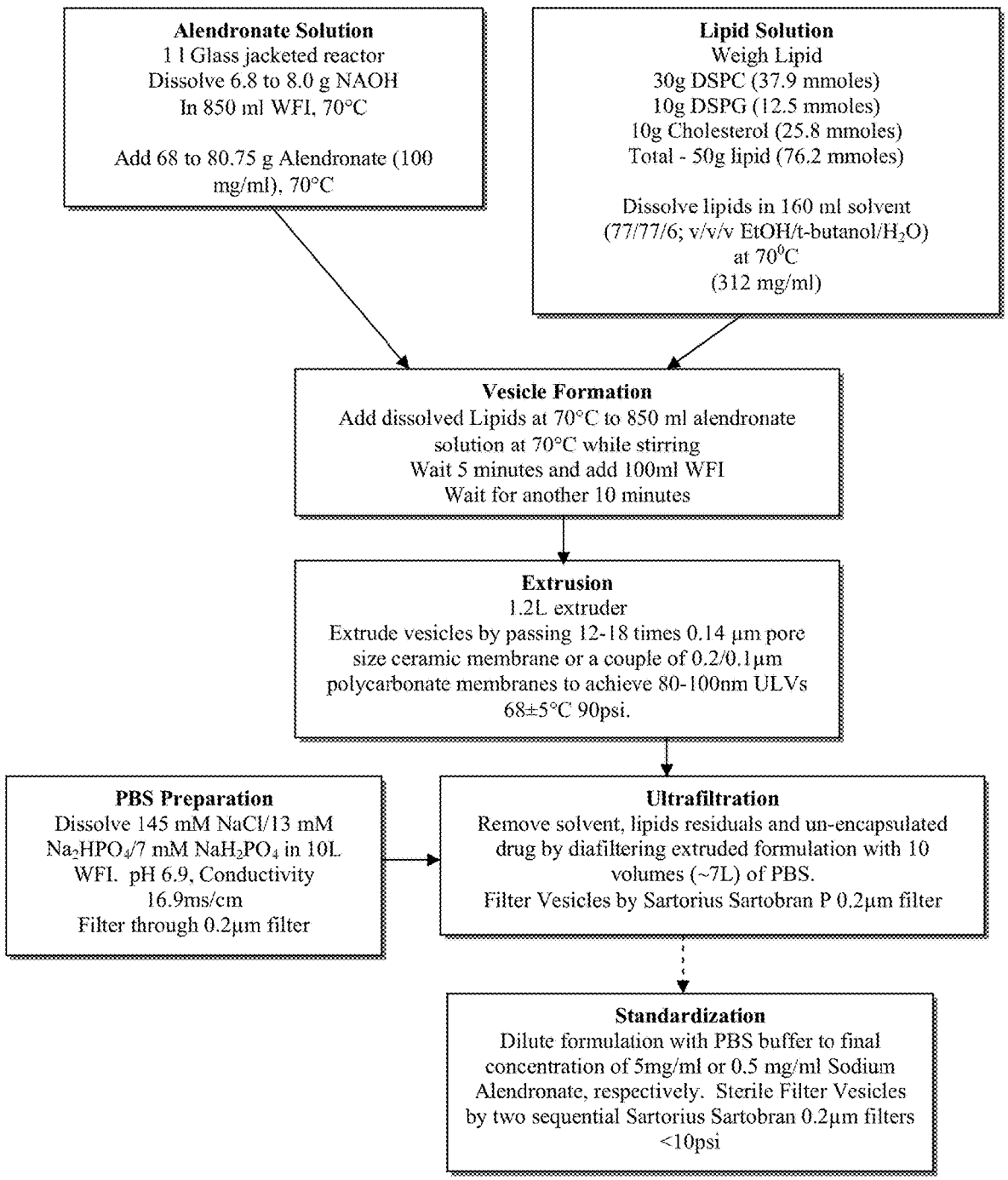
FIG. 2 represents a flow-chart summarizing the manufacturing process of 1 liter of liposomal alendronate for IV infusion for dosage strength 5 mg/ml, and its process control parameters according to one aspect of the invention.

FIG. 2 represents a flow-chart summarizing the manufacturing process of 1 liter of liposomal alendronate for IV infusion for dosage strength 5 mg/ml, and its process control parameters. The manufacturing process for the 0.5 mg/ml dosage strength is the same as for the 5 mg/ml dosage strength. Only the final standardization step differs in forming a different final formulation concentration for administration. The skilled person in the art understands that other dosages may be manufactured pursuant to this process without undue experimentation.

The therapeutic agent solution (alendronate solution) and lipid solution were prepared as follows:

Alendronate Solution.

NaOH (6.8-8.0 g) was weighed and dissolved in 850 ml water for injection (WFI), with temperature at 70±3° C., 600±150 RPM. Complete dissolution was verified by visual inspection. Sodium Alendronate (68 to 80.75 g) was dissolved in the NaOH solution, with temperature at 70±3° C., stirring at 600±150 RPM. Complete dissolution was verified by visual inspection (i.e., clear solution), conductivity and pH measurements were verified (pH=6.8±0.3. Conductivity=18.0±1 ms/cm).

Lipid Solution.

Lipids comprising 30 g DSPC (37.9 mmoles), 10 g DSPG (12.5 mmoles), and 10 g cholesterol (25.8 mmoles) (DSPC/DSPG/Cholesterol; 3/1/2 mol/mol/mol) were weighed and dissolved in a 250 ml beaker on a heated magnetic stirrer in 160 ml of t-butanol/EtOH/$H_2O$ (77/77/6, v/v/v) at temperature of 70±3° C., forming a lipid solution with a concentration of 312 mg/ml. A clear yellow solution was formed once the temperature was within limits.

MLV Formulation.

The lipid solution was added to the alendronate solution (1 part drug; 5.3 parts lipid) while mixing at 600+150 RPM and maintaining temperature 70±3° C. After at least 5 minutes, 100 ml WFI (10% of total volume) was added to reduce solvent concentration before extrusion. The formulation was mixed for additional 10 minutes.

Extrusion.

The formulation was subjected to extrusion by 1.2 L heated stainless steel extruder assembled with one 0.14 µm ceramic membrane or with two polycarbonate membranes (e.g., a 0.2 pre-filter and 0.1 µm membrane) to reduce the size of the vesicles and improve the vesicle homogeneity at pressure=90±15 psi and temperature=68±5° C. The process required 12-18 passes to achieve vesicles of 80-100 nm. Extrusion passes were sampled in real time to verify vesicle size before ultrafiltration. The liposome formulation size was analyzed using Malvern Nano ZS analyzer (acceptance limits: 95±20 nm). An extrusion sample was also analyzed for aerobic bacterial count (bio-burden control). The acceptance limit was <100 CFU/ml.

Ultrafiltration and Diafiltration.

First, the formulation was allowed to cool to <45° C. before undergoing ultrafiltration. Ultrafiltration was performed on Amersham QuixStand system with a 500K hollow fiber membrane. The formulation was concentrated using an inlet pressure not exceeding 25 psi. Upon reaching a minimal volume, the formulation was dialyzed with 10 initial volumes (~7 L) of a phosphate buffer saline (PBS) solution. The PBS solution was prepared by dissolving 145 mM NaCl, 13 mM $Na_2HPO_4$, and 7 mM $NaH_2PO_4$ in 10 L WFI. The PBS had pH about 6.9 and conductivity about 16.9 ms/cm. The PBS was filtered through a 0.2 µm filter. Diafiltration end was marked by measuring the pH and conductivity of the dialyzed formulation The formulation was drained from the ultrafiltration system not exceeding 120% of initial volume (~1.2 liter). A sample was taken for general analysis and for aerobic bacterial count (bio-burden control). The acceptance limit was <1,000 CFU/ml.

At the end of dialysis, the formulation was filtered through 0.2 µm filter to maintain bio-burden control. A pressure vessel containing the formulation was connected to a sterile 0.2 µm filter (Sartorius Sartobran P). The filter was pre-assembled to a sterile reception tank. Filtration is performed by applying pressure of 5-30 psi on the pressure vessel. A sample was taken for general analysis and for aerobic bacterial count (bio-burden control). The acceptance limit was <100 CFU/ml.

Final Standardization.

The formulation was analyzed for size, lipid/therapeutic agent composition in the liposome, drug and free therapeutic agent content by HPLC. The expected yield in this example was a one liter formulation containing about 6 mg/ml encapsulated alendronate and 35 mg/ml lipids. Based on the results of the alendronate concentration, the required dilution was calculated to achieve about one liter of final formulation concentration of 5 mg/ml or 0.5 mg/ml. To produce the 5 mg/ml formulation, about 900 ml liposomal alendronate after ultrafiltration were diluted with about 100 ml PBS, prepared as described above. Additionally, to produce the 0.5 mg/ml formulation, about 100 ml liposomal alendronate after ultrafiltration were diluted with about 900 ml PBS for 0.5 mg/ml concentration. A sample was taken to determine the achieved concentration of alendronate.

Following the production of the standard formulation concentration, a bottle containing the formulation was connected to two sequential sterile 0.2 µm filters (Sartorius Sartobran P) located in a class 100 room or a sterile biological hood. The filter was pre-assembled to a pre-sterilized disposable reception bag or bottle. Filtration was performed by a peristaltic pump or pressurized nitrogen. Pressure should not exceed 10 psi. When filtration was ended the filter was tested for integrity.

The liposome alendronate for IV infusion produced in the above example had a number of desirable properties, for example (i) three year stability of at least the alendronate and lipids at 5° (range 2-8° C.); (ii) average vesicle diameter of 80±5 with no particulate matter; (iii) a concentration of alendronate sodium of up to 5 mg/ml (range 0.1-5.0 mg/ml); (iv) alendronate encapsulation greater than or equal to 96%; (v) lipid composition of distearoyl phosphatidylcholine/distearoyl phosphatidylglycerol/cholesterol (DSPC/DSPG/CHOL) of 3/1/2 mol/mol/mol; (vi) physiological osmolality of 270-340 mO/kg, (vii) viscosity similar to water, i.e., dynamic viscosity of about 1.0 mPa s at 20° C.; (viii) pH 6.8 (range 6.8-7.0); (ix) worldwide acceptability of excipient quality in accordance with the US or EP Pharmacopeia; (x) meets USP guidelines for sterility and pyrogens as published in the USP 24-NF 19; (xi) compatibility (use) with saline, infusion kits and syringes; and (xii) compatibility (process) with filters, tubing stainless steel and glass.

Figure 3:
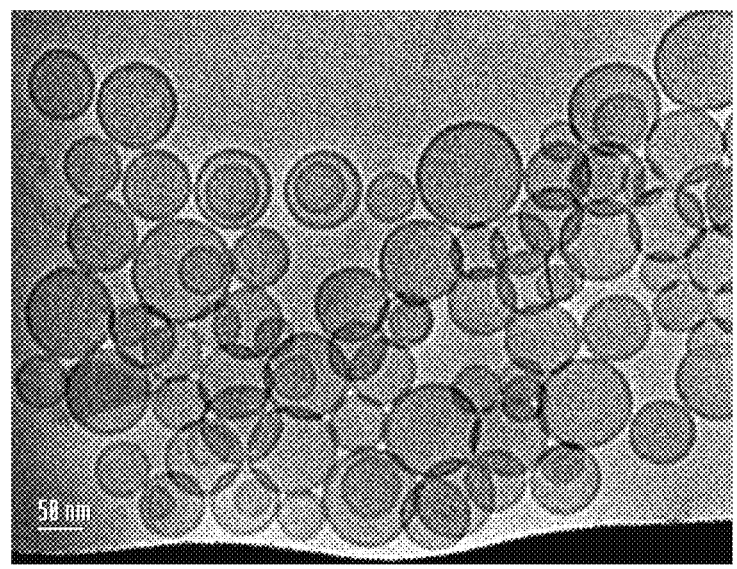
FIG. 3 is a TEM image of the liposomal alendronate according to one aspect of the invention.

FIG. 3 is a TEMS image of the liposomal alendronate manufactured in the example above. Good homogeneity and uniformity of the liposome population was observed, and the liposomes shown are sized between 40 and 120 nm.

Example 2—Liposome Rigidity Testing

Four samples of large unilamellar liposomes (diameter approx. 100 nm) were analyzed for rigidity. Empty liposomes dissolved in PBS made in accordance with the present invention were labeled LPO. Liposome formulations containing 5.0 mg/ml of alendronate made in accordance with the present invention were labeled as LSA. Two other liposome samples, labeled KS and HU, dissolved in HEPES, were made in accordance with the prior art method described in Epstein-Barash, Hila, et al., "Physicochemical parameters affecting liposomal bisphosphonates bioactivity for restenosis therapy: Internalization, cell inhibition, activation of cytokines and complement, and mechanism of cell death", J. Controlled Release 146 (2010) 182-195

Each sample was analyzed for specific volume compressibility of liposomes. Using ultrasound velocimetry, the elastic properties of the liposomes was evaluated based on the following relationship:

$$B_S = \frac{1}{\rho \cdot u^2}, \quad (1)$$

where βs, ρ, and u are the adiabatic compressibility, the density, and the sound velocity of the suspension, respectively. Hianik T., Haburcak M., Lohner K., Prenner E., Paltauf F., Hermetter A. (1998): Compressibility and density of lipid bilayers composed of polyunsaturated phospholipids and cholesterol, Coll. Surf. A 139, 189-197; Hianik T., Rybár P., Krivánek R. Petríková M., Milena Roudna M. Hans-Jürgen Apell, H J. (2011): Specific volume and compressibility of bilayer lipid membranes with incorporated Na, K-ATPase. Gen. Physiol. Biophys. 30, 145-153. Thus, by measuring the changes of sound velocity and density, the changes of compressibility can also be determined.

Ultrasound velocity was measured using a fixed-path differential velocimeter consisting of two almost identical acoustic cavity resonators (Sarvazyan A. P. (1991): Ultrasonic velocimetry of biological compounds, Annu. Rev. Biophys. Biophys. Chem. 20, 321-342; Sarvazyan A. P., Chalikian T. V. (1991): Theoretical analysis of an ultrasonic interferometer for precise measurements at high pressures, Ultrasonics 29, 119-124) operated at frequencies around 7.2 MHz. The resonance frequencies of the cells were measured using a computer-controlled network analyzer (USAT, USA). The sample volume was 0.7 ml. The resonator cells were equipped with magnetic stirrers to ensure homogeneously dispersed samples during the measurements. One resonator contained the liposome solution in a concentration 10 mg/ml in respect of phospholipids, whereas the other one was filled with the same buffer solution (PBS or HEPES) without vesicles as reference. When starting a series of measurements, first the resonance frequencies of both resonators were compared by measuring both cells with identical reference liquid. As the energy density of the sonic signal was small throughout (the pressure amplitude in the ultrasonic wave was less than 103 Pa), any effects of the sound wave on the structural properties of the vesicles were avoided. In general, ultrasonic velocimetry allows the determination of the sound velocity [u] or rather its concentration-dependent increments (Sarvazyan A. P. (1982): Development of methods of precise measurements in small volumes of liquids, Ultrasonics 20, 151-154) as defined by the equation:

$$[u] = \frac{u - u_0}{u_0 c}, \quad (2)$$

where c is the solute concentration in mg/ml, and the subscript "0" refers to the solvent (buffer). The value [u] can be directly determined from the changes of resonance frequencies f and $f_0$ of both resonators (f is resonance frequency of the sample, and $f_0$ that of the reference-buffer):

$$[u] = \frac{u - u_0}{u_0 c} = \frac{f - f_0}{f_o c}(1 + \gamma) \quad (3)$$

(the coefficient fulfills the condition $\gamma \ll 1$ and can be neglected in the calculations).

A high precision densitometric system (DMA 60 with two DMA 602 M sample chambers, Anton Paar K G, Graz, Austria) operating according to the vibrating tube principle (Kratky O., Leopold H., Stabinger H. (1973): The determination of the partial specific volume of proteins by the mechanical oscillator technique, In: Methods in Enzymology (Ed. E. Grell), vol. 27, pp. 98-110, Academic Press, London) was used to determine the density ($\rho$) of the vesicle solution. Apparent specific partial volumes ($\varphi V$) were calculated from the density data using the equation:

$$\varphi_V = \left[1 - \frac{\rho - \rho_0}{c}\right] \cdot \frac{1}{\rho_0} = \frac{1}{\rho_0} - [\rho]. \quad (4)$$

where the subscript 0 refers again to the reference solvent and $[\rho]=(\rho-\rho_0)/(\rho_0 c)$ denotes the concentration increment of density. The temperature of the cells was controlled to within ±0.02° C. with a Lauda R K 8 CS ultra-thermostat (Lauda, Germany).

The determination of the specific volume in addition to the sound-velocity concentration increment allowed the estimation of the reduced specific apparent compressibility, $\varphi_K/\beta_0$, of the vesicles, based on the following equation:

$$\frac{\varphi_K}{\beta_0} = -2[u] - \frac{1}{\rho_0} + 2\varphi_V, \quad (5)$$

where $\beta_0$ is the coefficient of the compressibility and po is the buffer density (Sarvazyan 1991). The value of $\varphi_K/\beta_0$ indicates the volume compressibility of the liposomes relative to the buffer. The higher value of $\varphi_K/\beta_0$ means higher compressibility (i.e. less rigidity) of liposomes.

In order to determine specific volume compressibility of liposomes, the concentration increment of ultrasound velocity, [u], and density, $\rho$, were measured. Then, the specific volume, $\varphi V$, and specific apparent compressibility, $\varphi_K/\beta_0$ were determined by means of equations (4,5).

Figure 4:
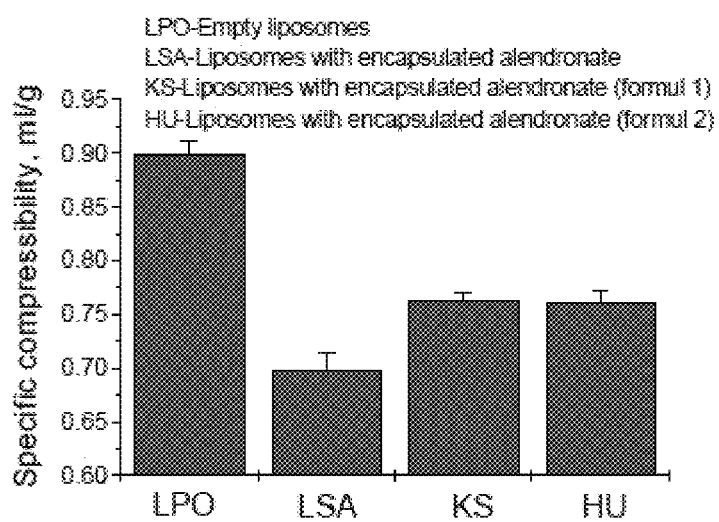
FIG. 4 is a graph comparing the specific compressibility of various liposome formulations.

FIG. 4 demonstrates that the liposomes of the present invention are substantially rigid in comparison to other liposome formulations and empty liposomes. As shown in FIG. 4, the specific compressibility (inverse to rigidity) of the LSA liposomes are significantly lower than that of empty liposomes of those made by conventional prior art formulations. The compressibility of the LSA liposomes is around 0.70, while that of the empty liposome is around 0.90. The specific compressibility of the KS and HU liposomes are significantly different at 0.75. This example demonstrates that mechanical properties is sensitive to the formulation and the presence of drug inside the liposomes.

Example 3—Liposome Stability Analysis

The stability of the liposome formulation made in accordance with Example 1 is exemplified in Tables 4 and 5. Table 4 demonstrates that the liposomes of the current invention are stable when stored at 4 degrees C. at least through 36 months, and the formulation meets all required specifications.

TABLE 4

| | Stability at 4 C. | | | | | | |
|---|---|---|---|---|---|---|---|
| | Spec | Base | 1 Mo | 7 Mo | 12 Mo | 24 Mo | 36 Mo |
| appearance | whitish dispersion | conform | conform | conform | conform | conform | conform |
| Alendronate (mg/ml) | 0.5 ± 0.05 | 0.49 | 0.53 | 0.54 | 0.51 | 0.52 | 0.52 |
| Encapsulation Percentage (%) | >96 | 98% | 98% | 96 | >98% | >99% | >99% |
| DSPC (mg/ml) | 1.4-2.0 | 1.9 | 1.8 | 2 | 1.6 | 1.8 | 1.8 |

TABLE 4-continued

Stability at 4 C.

| | Spec | Base | 1 Mo | 7 Mo | 12 Mo | 24 Mo | 36 Mo |
|---|---|---|---|---|---|---|---|
| DSPG (mg/ml) | 0.5-0.7 | 0.6 | 0.6 | 0.6 | 0.5 | 0.6 | 0.6 |
| Chol. (mg/ml) | 0.5-0.7 | 0.55 | 0.59 | 0.56 | 0.58 | 0.6 | 0.61 |
| drug:lipid ratio | 1:5.7 ± 1.0 | 1; 6.2 | 1; 5.6 | 1; 5.9 | 1; 5.3 | 1; 5.8 | 1; 5.8 |
| vesicles size (nm) | diameter 100 ± 30 | 92 nm | 92 nm | 92 nm | 92 nm | 91 nm | 91 nm |
| pH | 6.7-7.3 | 6.9 | 6.9 | 6.9 | 7 | 7 | 6.9 |
| osmolality (mo/kg) | 270-340 | 309 | na | 317 | 316 | 312 | 312 |

Table 5 demonstrates that the liposomes of the current invention are stable when stored at 25 degrees C. at least through 7 months, and the formulation meets all required specifications.

TABLE 5

Stability at 25 C.

| | Spec | Base | 1 Mo | 2 Mo | 7 Mo |
|---|---|---|---|---|---|
| appearance | whitish dispersion | conform | conform | conform | conform |
| Alendronate (mg/ml) | 0.5 + 0.05 | 0.49 | 0.52 | 0.51 | 0.51 |
| Encapsulation Percentage (%) | >96 | 98% | 98 | >99 | 98 |
| DSPC (mg/ml) | 1.4-2.0 | 1.9 | 1.9 | 1.9 | 1.9 |
| DSPG (mg/ml) | 0.5-0.7 | 0.6 | 0.6 | 0.6 | 0.6 |
| Chol. (mg/ml) | 0.5-0.7 | 0.55 | 0.59 | 0.58 | 0.57 |
| drug:lipid ratio | 1:5.7 + 1.0 | | | | 01:06.0 |
| vesicles size | diameter 100 + 30 | 92 nm | 92 | 92 | 93 |
| pH | 6.7-7.3 | 6.9 | 7 | 6.9 | 6.9 |
| osmolality | 270-340 | 309 | na | na | 315 |

Example 4—Liposome Uniformity Analysis

The uniformity of the liposome formulation by assayed using the Malvern Nano zs particle sizing system. This procedure determines the uniformity of the vesicle size of liposomal formulation by Dynamic Light Scattering (DLS) and characterizes the size distribution of particles suspended in liquid media. This technique is sensitive to particle size distribution in the range of 10-1000 nm, and is useful for a range of particles including liposomes emulsions, nanoparticles and synthetic polymers. The technique can be used to provide an average diameter of a homogeneous liposome preparation, as well as an indication of formulation heterogeneity. After standardizing the Malvern Nano-zs particle size system pursuant to the operating instructions, liposome samples of 0.5 mg/ml were first diluted by ⅓ in PBS. The UV λmax 600 nm of the diluted solution was confirmed using Ultraspec 2100pro UV/VIS Spectrophotometer. The liposome sample was diluted again until optical density (O.D.) value of 0.10±0.02 is achieved. Again, the UV λmax 600 nm of the second dilution solution was confirmed have a 0.10±0.02 O.D value. Then, 1.0-1.5 ml of the diluted sample is placed in a culture tube, and analyzed for vesicle size by Malvern Nano-zs particle size system. Analysis is carried out at ambient temperature (23° C.±2° C.) at fixed angle 173°, laser wavelength 633 nm. Data is accumulated to achieve 150-500 Kcps (kilo counts per second).

Table 6 illustrates the measurements of a formulation made in accordance with this invention. The average liposome size is 80.41 nm, with a PDI of 0.04.

TABLE 6

| Measurement # | Size (nm) | PDI |
|---|---|---|
| 1 | 80.28 | 0.042 |
| 2 | 80.49 | 0.024 |
| 3 | 80.29 | 0.052 |
| 4 | 80.82 | 0.022 |
| 5 | 80.69 | 0.041 |
| 6 | 79.68 | 0.042 |
| 7 | 80.57 | 0.043 |
| 8 | 80.56 | 0.030 |
| 9 | 80.33 | 0.028 |
| Average | 80.41 | 0.04 |
| STDEV | 0.330 | 0.010 |
| RSD % | 0.41 | 28.50 |

HU liposomes, prior art liposomes described in Example 2 above, were analyzed for uniformity pursuant to the above-described procedure. The Z-Average size of the HU liposomes was 176.5 nm.

Figure 5A:
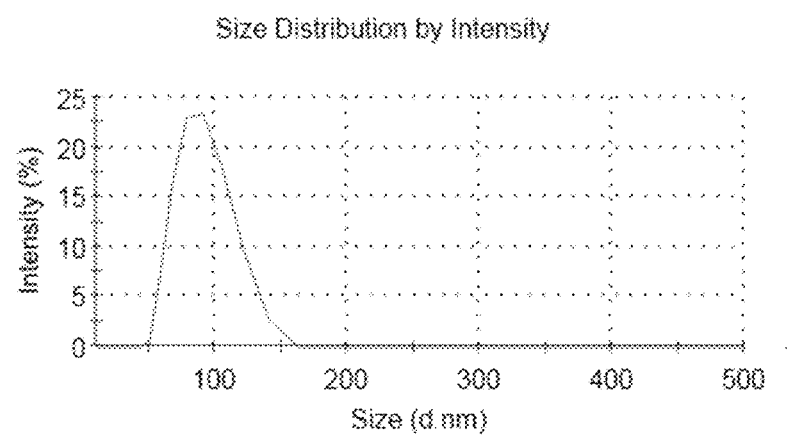
FIG. 5A is a graph of the size distribution of the liposome formulation of the invention.
Figure 5B:
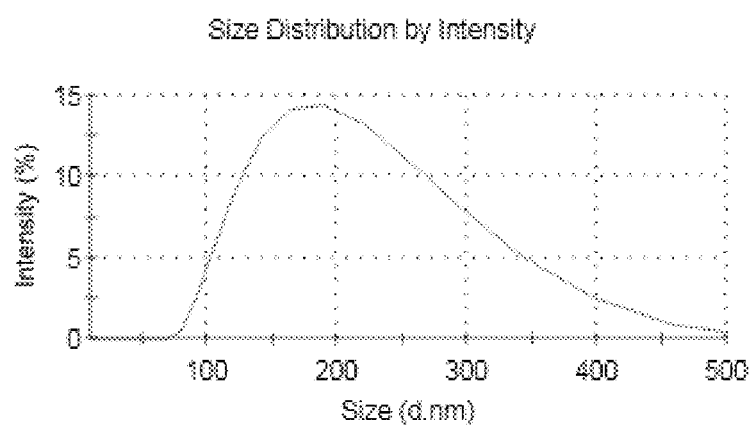
FIG. 5B is a graph of the size distribution of a liposome formulation in the art.

FIGS. 5A and 5B illustrate the size distribution of the liposomes made in accordance with this invention and HU liposomes, respectively. FIG. 5A shows that the liposome formulation of the invention have a mean diameter approximately 88 nm, and the diameter size tightly ranges from 69 to 107 nm. In contrast, FIG. 5B shows that the HU liposome formulation have a mean diameter around 201 nm, with liposomes having diameters from as low as 80 nm to as large as 500 nm. The PDI of the formulation in FIG. 5A was 0.025. The PDI of the HU formulation of FIG. 5B was 0.118.

The contents of all published articles, books, reference manuals, and abstracts as cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A liposome having a lipid ingredient and encapsulating a therapeutic agent, wherein a mass ratio of said therapeutic agent to lipid ingredient is about 1:5 to 1:8, wherein the lipid ingredient comprises a phospholipid and cholesterol, the lipid ingredient comprising at least 20 molar percentage cholesterol, and wherein the liposome has osmolality internal to the liposome in a range of 340-440 mO/kg.

2. A formulation comprising a liposome, said liposome having a lipid ingredient and a therapeutic agent, a mass ratio of the therapeutic agent to lipid ingredient being about 1:5 to 1:8, wherein the lipid ingredient comprises a phospholipid and cholesterol, the lipid ingredient comprising at least 20 molar percentage cholesterol, and wherein the liposome has osmolality internal to the liposome in a range of 340-440 mO/kg.

3. The liposome of claim 1 or 2, wherein the lipid ingredient comprises DSPC, DSPG and the cholesterol in a molar ratio of about 3:1:2.

4. The liposome of claim 1 or 2, wherein the therapeutic agent comprises one of a cytotoxic and cytostatic agent, the therapeutic agent selected from the group consisting essentially of: gallium, gold, silica, 5-fluorouracil, cisplatin, alkylating agents, mithramycin and paclitaxel.

5. The liposome of claim 1 or 2, wherein the therapeutic agent at least one of decreases activity and amount of phagocytic cells.

6. The liposome of claim 1 or 2, wherein said liposome has compressibility less than 0.70 ml/g.

7. The liposome of claim 1 or 2, wherein the liposome has osmolality external to the liposome in a range of 270-340 mO/kg, and wherein the liposome has conductivity internal to the liposome in a range of 13.5-17.5 ms/cm.

8. The liposome of claim 1 or 2, wherein the therapeutic agent is a bisphosphonate.

9. The liposome of claim 8, wherein the bisphosphonate has a bisphosphonate concentration range of 0.1 to 5 mg/ml within the liposome.

10. The liposome of claim 8, wherein the bisphosphonate comprises a compound having formula (I):

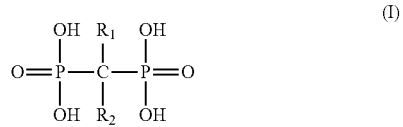

wherein $R_1$ is H, OH or halogen group; and
$R_2$ is halogen; linear or branched $C_1$-$C_{10}$ alkyl or $C_2$-$C_{10}$ alkenyl, optionally substituted by heteroaryl or heterocyclyl alkylamino or $C_3$-$C_8$ cycloalkylamino; —NHY where Y is hydrogen, $C_3$-$C_8$ cycloalkyl, aryl or heteroaryl; or —SZ, where Z is chlorosubstituted phenyl or pyridinyl.

11. The liposome of claim 8, wherein the bisphosphonate is selected from the group consisting of: clodronate, etidronate, tiludronate, alendronate and risendronate.

12. The liposome of claim 1 or 2, wherein the liposome has an internal liposomal pH in a range of 6.8-7.0.

13. The liposome of claim 1 or 2, wherein the liposome has an average size of about 80±5 nm.

14. The liposome of claim 1 or 2, wherein the liposome is stable when stored at one of: 25° C. for at least 7 months, and stable when stored at 2-8° C. for at least 36 months.

15. The liposome of claim 1 or 2, wherein the liposome has a dynamic viscosity of about 1.0 mPas at 20° C.

16. The formulation of claim 2, wherein the formulation comprises less than 4% unencapsulated therapeutic agent.

17. The formulation of claim 2, wherein the formulation has a Poly Dispersity Index less than 0.075.

18. The formulation of claim 17, wherein the Poly Dispersity Index is between 0.02 and 0.05.

19. The liposome of claim 1 or 2, wherein the liposome has an osmolality external to the liposome in a range different than the range for the osmolality internal to the liposome.

* * * * *